US010500221B2

(12) United States Patent
Chassagne et al.

(10) Patent No.: US 10,500,221 B2
(45) Date of Patent: Dec. 10, 2019

(54) CRYSTALLINE DIFUCOSYLLACTOSE

(71) Applicant: Glycom A/S, Hørsholm (DK)

(72) Inventors: Pierre Chassagne, Beaumont (FR);
Martin Matwiejuk, Hamburg (DE);
Markus Hederos, Svedala (SE);
Györgyi Osztrovszky, Kisvárda (HU);
Gyula Dekany, Sinnamon Park (AU)

(73) Assignee: Glycom A/S, Hørsholm (DK)

( * ) Notice: Subject to any disclaimer, the term of this patent is extended or adjusted under 35 U.S.C. 154(b) by 65 days.

(21) Appl. No.: 15/532,747

(22) PCT Filed: Dec. 4, 2015

(86) PCT No.: PCT/DK2015/050382
§ 371 (c)(1),
(2) Date: Jun. 2, 2017

(87) PCT Pub. No.: WO2016/086947
PCT Pub. Date: Jun. 9, 2016

(65) Prior Publication Data
US 2017/0340654 A1 Nov. 30, 2017

(30) Foreign Application Priority Data
Dec. 5, 2014 (DK) .................................. 2014 70763

(51) Int. Cl.
| | | |
|---|---|---|
| A61K 31/702 | (2006.01) | |
| C07H 1/06 | (2006.01) | |
| C07H 3/06 | (2006.01) | |
| C07H 15/18 | (2006.01) | |
| A61K 31/7024 | (2006.01) | |

(52) U.S. Cl.
CPC ........ *A61K 31/702* (2013.01); *A61K 31/7024* (2013.01); *C07H 1/06* (2013.01); *C07H 3/06* (2013.01); *C07H 15/18* (2013.01); *Y02A 50/473* (2018.01)

(58) Field of Classification Search
None
See application file for complete search history.

(56) References Cited

U.S. PATENT DOCUMENTS

| | | | |
|---|---|---|---|
| 4,652,640 A | 3/1987 | Sakai et al. | |
| 7,521,212 B1 | 4/2009 | Samain et al. | |
| 2013/0172548 A1* | 7/2013 | Dekany .................... | C07H 1/06 536/123.1 |
| 2014/0234912 A1* | 8/2014 | Dekany .................. | C07H 17/02 435/99 |

FOREIGN PATENT DOCUMENTS

| | | |
|---|---|---|
| EP | 2896628 A1 | 7/2015 |
| WO | 9956754 A1 | 11/1999 |
| WO | 0104341 A1 | 1/2001 |
| WO | 2010115934 A1 | 10/2010 |
| WO | 2010115935 A1 | 10/2010 |
| WO | 2011100980 A1 | 8/2011 |
| WO | 2011150939 A1 | 12/2011 |
| WO | 2012112777 A2 | 8/2012 |
| WO | 2012113404 A1 | 8/2012 |
| WO | 2012158517 A1 | 11/2012 |
| WO | 2013139344 A1 | 9/2013 |
| WO | 2014009921 A1 | 1/2014 |
| WO | 2014018596 A2 | 1/2014 |
| WO | 2014048439 A1 | 4/2014 |
| WO | 2014069625 A1 | 5/2014 |
| WO | 2014075680 A1 | 5/2014 |
| WO | 2014086373 A1 | 6/2014 |
| WO | 2014090261 A1 | 6/2014 |
| WO | 2015032412 A1 | 3/2015 |

OTHER PUBLICATIONS

Kobata, The Journal of Biological Chemistry, vol. 247, No. 5, Mar. 10, pp. 1525-1529, 1972. (Year: 1972).*
Nishimoto, Bioscience, Biotechnology, and Biochemistry, 71:8, 2101-2104, 2007. (Year: 2007).*
Randriantsoa, M. (2008) "Synthese microbiologique des antigènes glucidiques des groupes sanguins." (Doctoral dissertation, Centre de Recherches sur les Macromolécules Végétales (CERMAV-CNRS)).
Chen, X, "Human Milk Oligosaccharides (HMOS): Structure, Function, and Enzyme-Catalyzed Synthesis," Advances in Carbohydrate Chemistry and Biochemistry, 2015, vol. 72, pp. 113-190.
Collins, P.M. (2006) Second Edition Dictionary of Carbohydrates with CD-ROM. Boca Raton, Florida: Chapman & Hall/CRC Taylor & Francis Group, p. 675.
Demchenko, A. (2008) Handbook of Chemical Glucosylation: Advances in Stereoselectivity and Therapeuric Relevance. Federal Republic of Germany: Wiley-VCH Verlag GmbH & Co. KGaA.
Drouillard, S. et al., "Large-Scale Synthesis of H-Antigen Oligosaccharides by Expressing Helicobacter pylori α1,2-Fucosyltransferase in Metabolically Engineered *Escherichia coli* Cell," Angew. Chem. Int. Ed., 2006, vol. 45, pp. 1778-1780.
Fernandez-Mayoralas, A. et al., "Synthesis of 3- and 2'-fucosyllactose and 3,2'-difucosyl-lactose from partially benzylated lactose derivatives," Carbohydrate Research, 1986, vol. 154, pp. 93-101.
Ishizuka Y., et al., "Three-Dimensional Structure of Fucosyllactoses in an Aqueous Solution," Journal of Carbohydrate Chemistry, 1999, vol. 18(5), pp. 523-533.
Samain, E. et al., "Production of O-acetylated and sulfated chitooligosaccharides by recombinant *Escherichia coli* strains harboring different combinations of nod genes," Journal of Biotechnology, 1999, vol. 72, pp. 33-47.
Takeo, K. et al., "Synthesis of lactodifucotetraose," Carbohydrate Research, 1985, vol. 141, pp. 159-164.
Tsukida, T, et al., "A Highly Practical Synthesis of Sulfated Lewis X: One-Pot, Two-Step Glycosylation Using "Armed/Disarmed" Coupling and Selective Benzoylation and Sulfation," J. Org. Chem., 1997, vol. 62, pp. 6876-6881.
Urashima, T. et al. (2011) Nutrition and Diet Research Progress: Milk Oligosaccharides. New York: Nova Science Publishers, Inc.
Caira, M.R. (1998) Crystalline Polymorphism of Organic Compounds. In: Weber E. et al. (eds) Design of Organic Solids. Topics in Current Chemistry, vol. 198. Springer, Berlin, Heidelberg, 46 pages.

* cited by examiner

*Primary Examiner* — Layla D Berry
(74) *Attorney, Agent, or Firm* — Neal, Gerber & Eisenberg LLP

(57) ABSTRACT

Crystalline difucosyllactose, useful in a pharmaceutical composition and a nutritional composition, is disclosed.

23 Claims, 5 Drawing Sheets

CRYSTALLINE DIFUCOSYLLACTOSE

CROSS-REFERENCE TO RELATED APPLICATIONS

This is a national stage entry pursuant to 35 U.S.C. § 371 of International Patent Application No. PCT/DK2015/050382, filed on Dec. 4, 2015, which claims priority to Denmark Patent Application No. PA 2014 70763 filed on Dec. 5, 2014, the contents of all of which are fully incorporated herein by reference.

FIELD OF THE INVENTION

This invention relates to the tetrasaccharide DFL (difucosyllactose, Fuc($\alpha$1-2)Gal($\beta$1-4)[Fuc($\alpha$1-3)]Glc) in crystalline form, its chemical synthesis and a method of obtaining it as a by-product in the production of 2'-FL (2'-O-fucosyllactose).

BACKGROUND OF THE INVENTION

In recent years, efforts have increasingly been made to produce industrially complex carbohydrates, such as secreted oligosaccharides. This has been due to the roles of such compounds in numerous biological processes in living organisms. Secreted oligosaccharides, such as human milk oligosaccharides ("HMOs"), have become particularly important commercial targets for nutrition and therapeutic applications. Human milk oligosaccharides (HMOs) have become of great interest in the past few years due to their important functions in human development. To date, the structures of at least 115 HMOs have been determined, and considerably more are probably present in human milk (Urashirna at al.: *Milk oligosaccharides*, Nova Science, 2011). Fucosylated lactoses including DFL are considered to be among the more important HMOs because of their nutritional value (see WO 2012/158517).

To date, ways of making large volumes of fucosylated lactoses at low cost have not been available. The isolation of fucosylated oligosaccharides from human milk has been rather difficult, even in milligram quantities, and very expensive due to the presence of a large number of other similar oligosaccharides in human milk. This problem has not been solved by current biotechnology or synthetic chemistry technology. Because of the growing commercial interest in nutritional compositions and supplements containing HMOs, there has been a need for a low cost method of making such HMOs.

Crystallization or recrystallization is one of the simplest and cheapest methods to separate a chemical product from contaminants and obtain it in pure form. In addition, crystalline modifications of a solid compound are important in the development of a compound, because different crystalline forms or polymorphs can have different properties—for example its thermodynamic stability, solubility, density, and hygroscopicity.

DFL was first isolated from mother's milk and its structure was elucidated with standard chemical methods including acid hydrolysis (Kuhn et al, *Liebigs Ann, Chem.* 611, 249 (1958)). Chemical synthesis of DFL has been disclosed by Takeo et al. (*Carbohydr. Res.* 141, 159 (1985)) and Fernandez-Mayoralas et al. (*Carbohydr. Res.* 154, 93 (1986)). The biosynthesis of DFL, together with 2'-FL and 3-FL (3-O-fucosyllactose), has been reported recently in NO 2012/112777. However, no crystalline form of DFL has, as yet, been described (Collins (ed.): *Dictionary of Carbohydrates*, Chapman & Hall/CRC (2006), p 675).

There has been a need, therefore, for a method of crystallizing DFL, particularly from a mixture of DFL and 2'-FL.

SUMMARY OF THE INVENTION

This invention provides DFL as a polycrystalline material containing water of hydration, preferably 2-5 cools of water per mol of DFL, particularly 5 mols of water per mol of DFL, and pharmacological or nutritional compositions containing the same.

The invention also provides a process for obtaining the crystalline DFL by crystallizing it from an aqueous solution and comprising the steps of:
  a) dissolving non-crystalline DFL in water or a solvent system containing one or more $C_1$-$C_4$ alcohols and water between room temperature (ca. 25° C.) and 80° C. to form a mixture, or providing a DFL solution in water or a solvent system containing one or more $C_1$-$C_4$ alcohols and water between room temperature (ca. 25° C.) and 80° C.,
  b) stirring the mixture obtained in step a) and allowing it to cool, preferably to room temperature, if step a) is performed above room temperature,
  c) optionally adding one or more $C_1$-$C_4$ alcohols to the mixture during step b), and
  d) then collecting and drying DFL crystals which precipitate from the mixture during step b) and/or c).

Advantageously, the process for obtaining the crystalline DFL comprises the steps of:
  a) dissolving non-crystalline DFL in a solvent system containing one or more $C_1$-$C_4$ alcohols and water between room temperature (ca. 25° C.) and 80° C. to form a mixture,
  b) stirring the mixture obtained in step a) and allowing it to cool, preferably to room temperature, if step a) is performed above room temperature,
  c) optionally adding seeding crystal of DFL to assist crystallization during step b),
  d) optionally adding one or more $C_1$-$C_4$ alcohols to the mixture during step b), and
  e) then collecting and drying DFL crystals which precipitate from the mixture during step b) and/or d).

The non-crystalline DFL used for crystallization is made by chemical or biotechnological method.

Furthermore, the invention relates to compounds of formula 1 and 2A

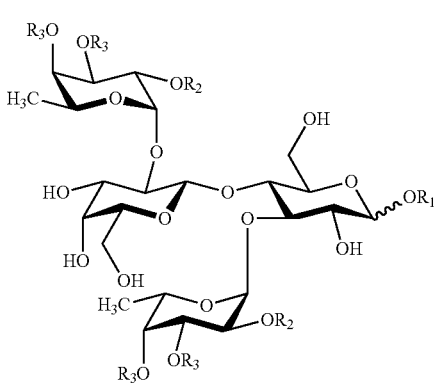

-continued

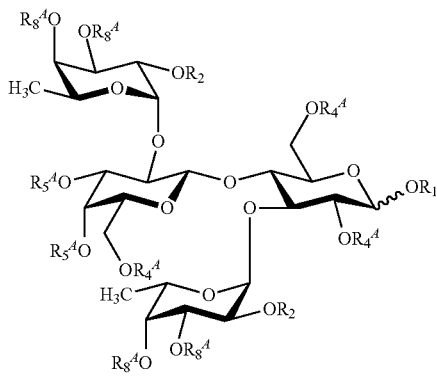

wherein R₁ and R₂ are independently a group removable by hydrogenolysis

R₃ is selected from a group removable by hydrogenolysis and H, preferably H, $R_4^A$ is selected from acyl and H, $R_5^A$ is selected from acyl and H, or two $R_5^A$ groups together form a moiety

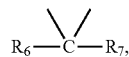

wherein R₆ and R₇ are independently selected from alkyl and phenyl, or R₆ and R₇ together with the carbon atom to which they are attached form a cycloalkylidene, and $R_8^A$ is selected from group removable by hydrogenolysis, acyl and H, or two $R_8^A$ groups belonging to same fucosyl residue together form a moiety

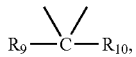

wherein R₉ and R₁₀ are independently selected from alkyl and phenyl, or R₉ and R₁₀ together with the carbon atom to which they are attached form a cycloalkylidene, provided that $R_4^A$, $R_5^A$ and $R_8^A$ are not all H, or a hydrate or solvate thereof.

Further, the invention relates to preparing DFL from a compound of formula 1 by hydrogenolysis.

BRIEF DESCRIPTION OF THE FIGURES

The invention will be described in further detail hereinafter with reference to the accompanying figures, in which.

DETAILED DESCRIPTION OF THE INVENTION

This invention provides DFL as a polycrystalline material. The crystalline DFL of this invention contains water of hydration, preferably 2-5 mols of water per mol of DFL, particularly 5 mols of water per mol of DFL, as determined from thermal gravimetric analysis of the sample.

Figure 1:
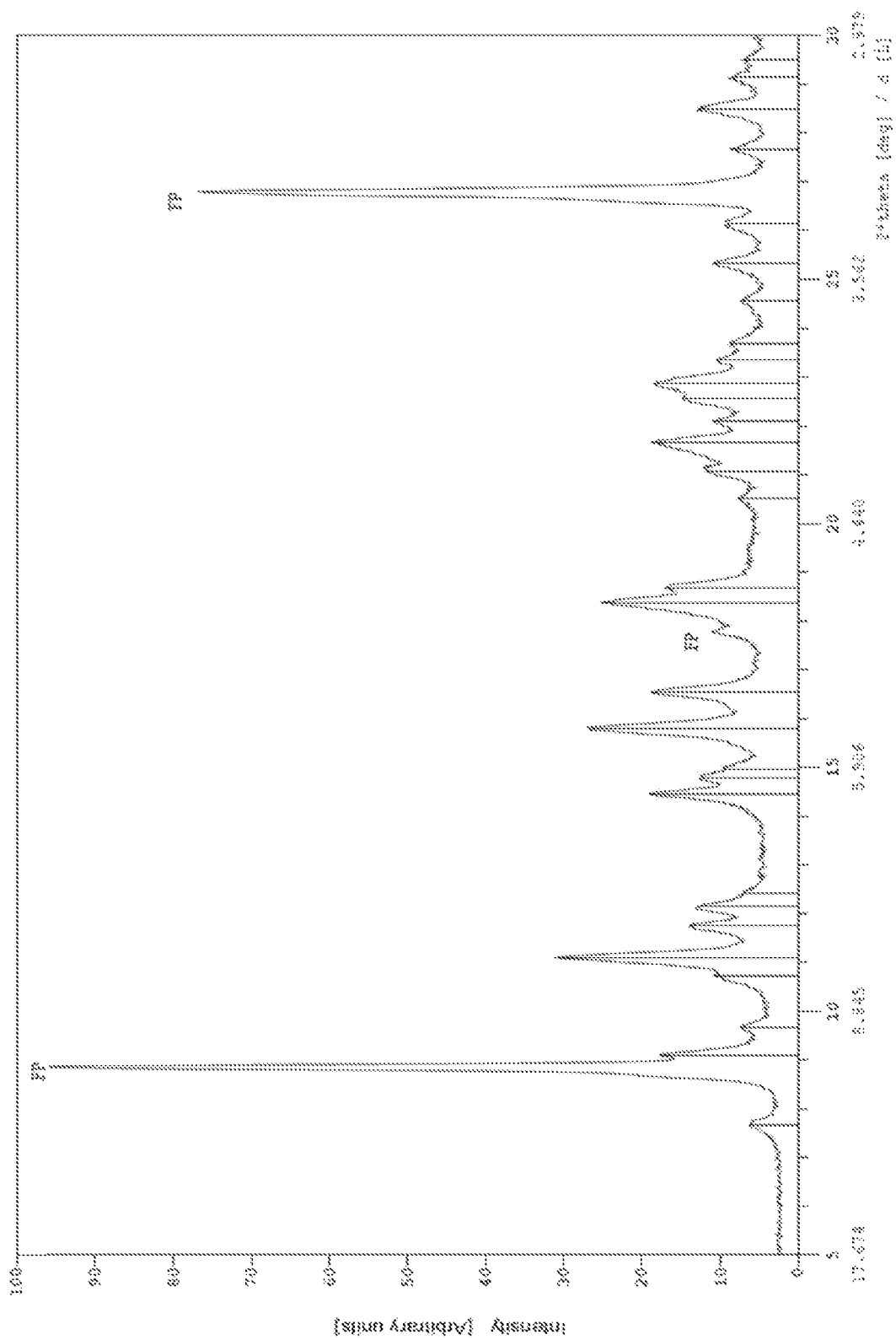
FIG. 1 shows the X-ray powder diffraction pattern of the crystalline difucosyllactose sample obtained according to Example 5C (Peaks marked with FP belong to fluorophlogopite internal standard).
Figure 2:
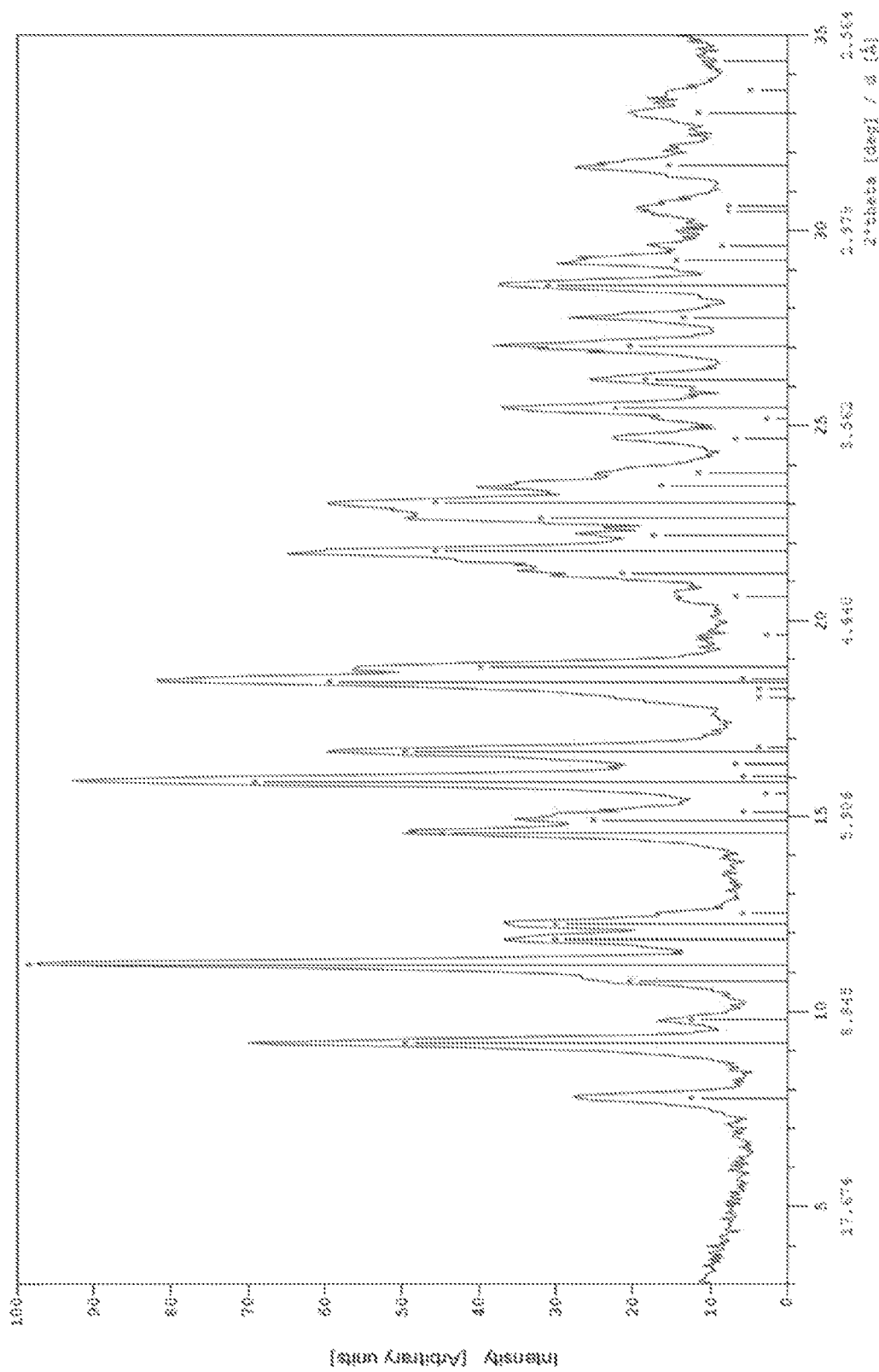
FIG. 2 shows the X-ray powder diffraction pattern of the crystalline difucosyllactose sample obtained according to Example 5A (compared to that of Example 5C marked with asterisk).
Figure 3:
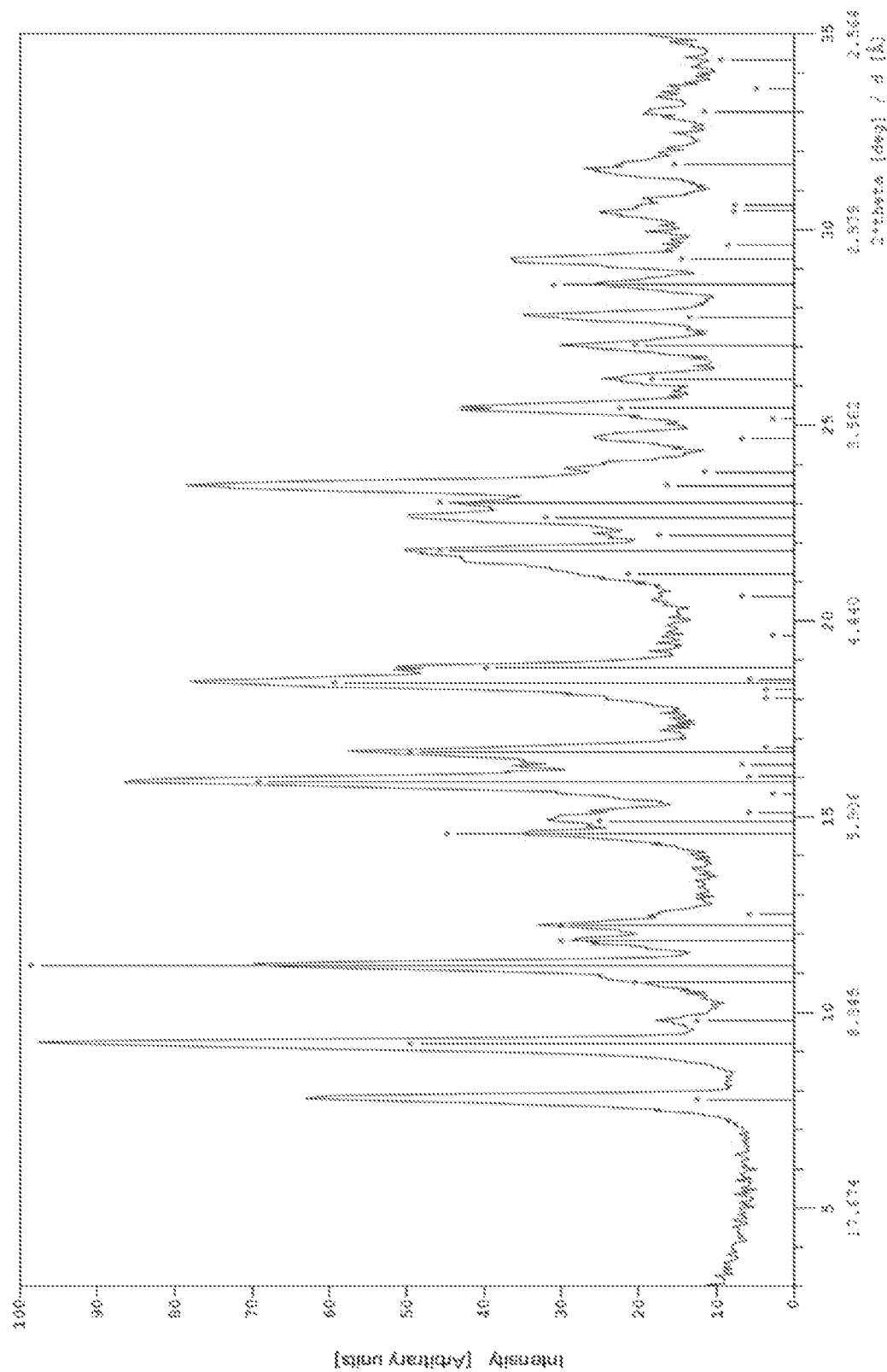
FIG. 3 shows the X-ray powder diffraction pattern of the crystalline difucosyllactose sample obtained according to Example 5B (compared to that of Example 5C marked with asterisk).
Figure 4:
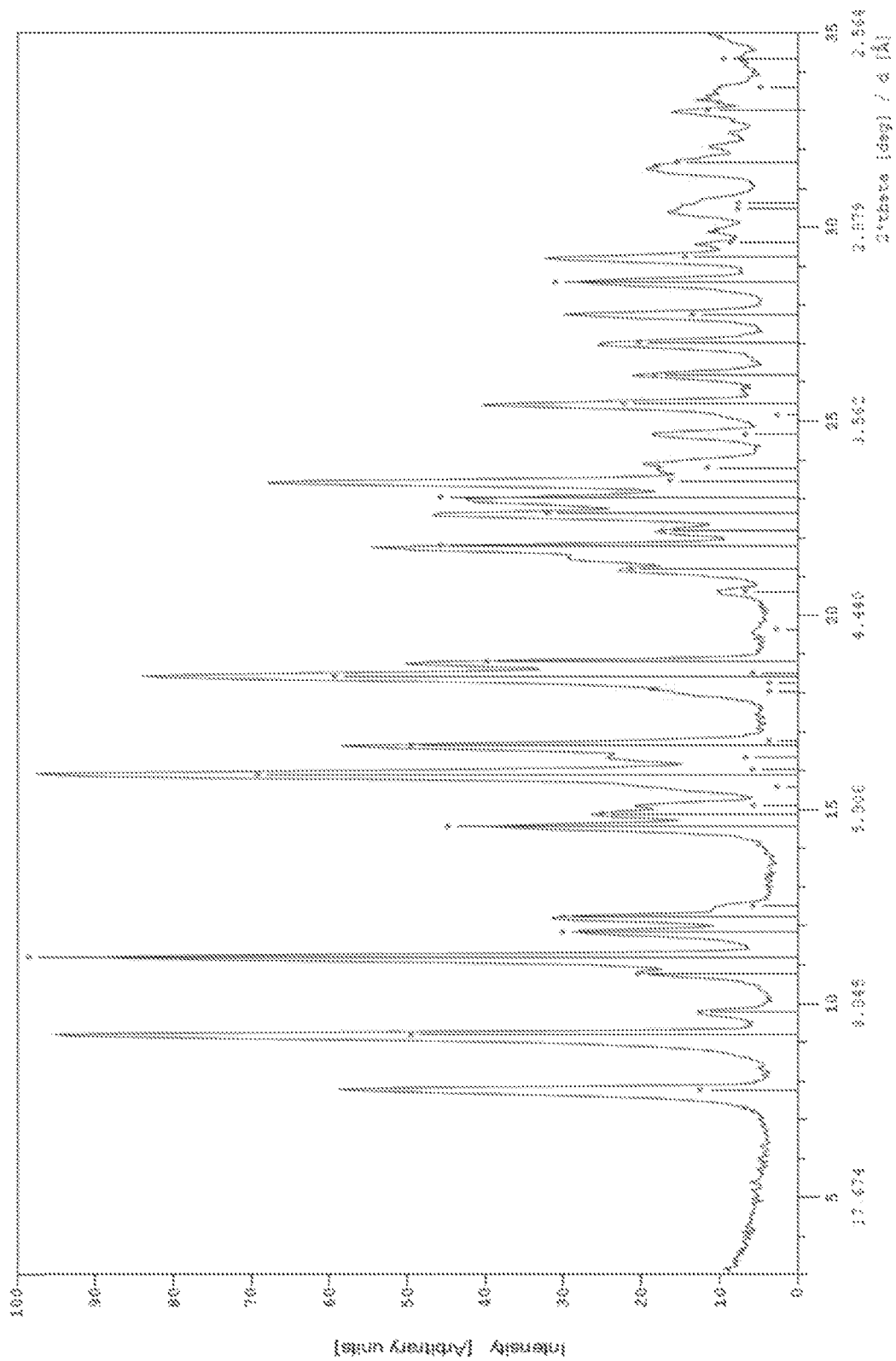
FIG. 4 shows the X-ray powder diffraction pattern of the crystalline difucosyllactose sample obtained according to Example 3A (compared to that of Example 5C marked with asterisk).
Figure 5:
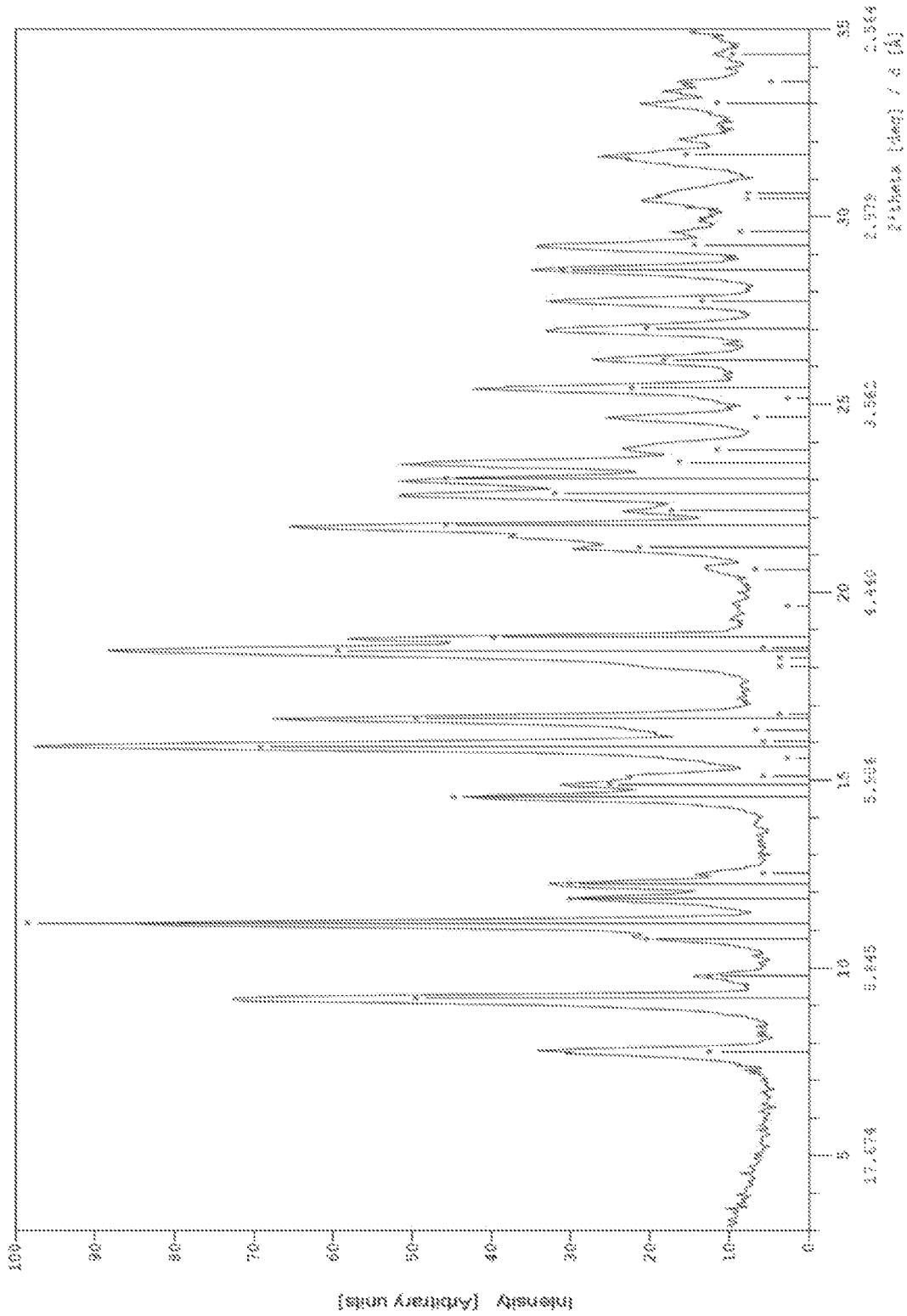
FIG. 5 shows the X-ray powder diffraction pattern of the crystalline difucosyllactose sample obtained according to Example 3B (compared to that of Example 5C marked with asterisk).

The crystalline DFL of this invention has an X-ray powder diffraction reflections, based on a measurement using CuKα radiation, at 11.10±0.20 2Θ, preferably at 11.10±0.20 2Θ and 15.80±0.20 2Θ, more preferably at 11.10±0.20 2Θ, 15.80±0.20 2Θ and 18.38±0.20 2Θ, and even more preferably at 11.10±0.20 2Θ, 15.80±0.20 2Θ, 18.38±0.20 2Θ and 14.46±0.20 2Θ, most preferably 11.10±0.20 2Θ, 15.80±0.20 2Θ, 18.38±0.20 2Θ, 14.46±0.20 2Θ and 16.54±0.20 2Θ, The XRPD pattern is shown in FIG. 1 and the list of peaks of the XRPD pattern of the crystalline DFL is set forth in Table 1, below.

TABLE 1

| 2Θ [deg] | rel. intensity (%) |
|---|---|
| 7.68 | 20 |
| 9.10 | 57 |
| 9.66 | 23 |
| 10.72 | 35 |
| 11.10 | 100 |
| 11.75 | 45 |
| 12.14 | 41 |
| 12.42 | 22 |
| 14.46 | 61 |
| 14.78 | 40 |
| 14.96 | 31 |
| 15.80 | 84 |
| 16.54 | 61 |
| 18.38 | 81 |
| 18.68 | 55 |
| 20.52 | 25 |
| 21.06 | 38 |
| 21.66 | 61 |
| 22.09 | 35 |
| 22.56 | 47 |
| 22.86 | 59 |
| 23.34 | 33 |
| 23.68 | 29 |
| 24.56 | 23 |
| 25.33 | 35 |
| 26.14 | 28 |
| 27.66 | 27 |
| 28.50 | 41 |
| 29.14 | 25 |

Preferably, the crystalline DFL is substantially pure. The term "substantially pure" preferably means herein that the crystalline DFL contains less than 10 w/w %, preferably less than 5 w/w %, more preferably less than 1 w/w %, even more preferably less than 0.5 w/w %, of impurities. The term "impurities" preferably means herein any physical entities different from the crystalline DFL and its water of hydration, such as an amorphous DFL, by-products, e.g. 2'-FL, from the synthesis of DFL, degradation products, inorganic salts and/or other contaminants.

Also preferably, the crystalline DFL is substantially free from organic solvents but contains water incorporated in the crystal structure. The term "substantially free from organic solvents" preferably means herein that the content of any organic solvent(s) is at most 1000 ppm, preferably at most 800 ppm, more preferably at most 600 ppm, even more preferably at most 400 ppm and in particular at most 200 ppm.

Of course, the crystalline DFL can be an anomeric mixture of α- and β-anomers or a pure form of one of the anomers.

The crystalline DFL of this invention is suitable for use as a pharmaceutical agent. Pharmaceutical compositions for such use can contain the crystalline DFL as an active ingredient and one or more conventional pharmaceutically acceptable carriers, as well as additives, adjuvants, excipients and diluents (water, gelatine, talc, sugars, starch, gum arabic, vegetable gums, vegetable oils, polyalkylene glycols, flavouring agents, preservatives, stabilizers, emulsifying agents, lubricants, colorants, fillers, wetting agents, etc.) as described in the standard reference text, Remington's Pharmaceutical Sciences. The amounts of such ingredients can vary depending on whether the pharmaceutical compositions are intended for use with infants, children or adults or subjects having specialized needs.

The crystalline DFL of this invention is also suitable also for nutritional use. Nutritional compositions, such as foods, drinks or feeds, for such use can contain the crystalline DFL as an active ingredient, together with other edible micronutrients, vitamins and minerals. The amounts of such ingredients can vary depending on whether the nutritional compositions are intended for use with normal, healthy infants, children, adults or subjects having specialized needs (e.g. suffering from metabolic disorders), Micronutrients include, for example, edible oils, fats or fatty acids (such as coconut oil, soy-bean oil, monoglycerides, diglycerides, palm olein, sunflower oil, fish oil, linoleic acid, linolenic acid etc.), carbohydrates (such as glucose, fructose, sucrose, maltodextrin, starch, hydrolysed cornstarch, etc.) and proteins from casein, soy-bean, whey or skim milk, or hydrolysates of these proteins, but protein from other sources (either intact or hydrolysed) can be used as well, Vitamins A, B1, B2, B5, B6, B12, C, D, E, H, K, folic acid, inositol and nicotinic acid and minerals and trace elements, such as Ca, P, K, Na, Cl, Mg, Mn, Fe, Cu, Zn, Se, Cr and I, can also be used.

A preferred nutritional composition containing the crystalline DFL is an infant formula, i.e., a foodstuff intended for use by infants during their first 4-6 months of life and satisfying by itself their nutritional requirements. The infant formula can contain one or more probiotic *Bifidobacterium* species, prebiotics such as fructooligosaccharides and galactooligosaccharides, proteins from casein, soy-bean, whey or skim milk, carbohydrates such as lactose, saccharose, maltodextrin, starch or mixtures thereof, lipids (e.g. palm olein, sunflower oil, safflower oil) and vitamins and minerals essential in a daily diet. The infant formula preferably contains 0.1-3.0 g of the crystalline DFL/100 g of the infant formula.

The crystalline DFL can also be used as a food supplement. The food supplement can also contain other active ingredients, such as one or more probiotics, vitamins, minerals, trace elements and other micronutrients. The food supplement can be for example in the form of tablets, capsules, pastilles or a liquid and contain conventional additives such as binders, coatings, emulsifiers, solubilising agents, encapsulating agents, film forming agents, adsorbents, carriers, fillers, dispersing agents, wetting agents, jellifying agents and gel forming agents. The daily dose of DFL can range from 0.1 to 3.0 g.

The crystalline DFL is further suitable for use as an active ingredient in the preparation of nutritional compositions including foods, drinks and feeds, preferably infant formulas, and food supplements. The nutritional compositions can be prepared in a conventional manner, for example by admixing micronutrient components in appropriate proportions, then adding vitamins and minerals. To avoid thermal degradation or decomposition, heat sensitive vitamins can be added after homogenization. Lipophilic vitamins can be dissolved in a fat source before mixing. A liquid mixture can made with water, the temperature of which is preferably about 50-80° C. to help dissolution or dispersal of the ingredients. The crystalline DFL polymorph can then be added. The resulting mixture can then be homogenized by flash heating to about 80-150° C. by steam injection, heat exchanger or autoclave. This thermal treatment also reduces significantly the bacterial loads. The hot mixture can then be cooled rapidly to about 60-80° C. If needed, further homogenization can be carried out at this temperature under high pressure of about 2-30 MPa. After cooling, heat sensitive constituents can then be added, and the pH and the content of the solids can be conveniently adjusted. The resulting mixture is then dried to a powder by, for example, conventional spray drying or freeze drying methods. Probiotics can then be added by dry-mixing.

This invention also provides a process A for obtaining the crystalline DFL by crystallizing it from an aqueous solution. The crystallization process comprises the steps of:
 a) dissolving non-crystalline DFL in water or a solvent system containing one or more $C_1$-$C_4$ alcohols and water between room temperature (ca. 25° C.) and 80° C. to form a mixture, or providing a DFL solution in water or a solvent system containing one or more $C_1$-$C_4$ alcohols and water between room temperature (ca. 25° C.) and 80° C.,
 b) stirring the mixture obtained in step a) and allowing it to cool, preferably to room temperature, if step a) is performed above room temperature,
 c) optionally adding one or more $C_1$-$C_4$ alcohols to the mixture during step b), and
 d) then collecting and drying DFL crystals which precipitate from the mixture during step b) and/or c).

In the description of this process A, the term "$C_1$-$C_4$ alcohol" preferably means a mono- or dihydroxy alkanes having 1 to 4 carbon atoms, such as methanol, ethanol, n-propanol, i-propanol, n-butanol, i-butanol, s-butanol, t-butanol, ethylene glycol, propylene glycol or a mixture of two or more of them. Preferred $C_1$-$C_4$ alcohols are $C_1$-$C_4$ monohydroxy alkanes such as methanol, ethanol, n-propanol, i-propanol, n-butanol, i-butanol, s-butanol and t-butanol and mixtures thereof. An even more preferred solvent system contains a $C_1$-$C_3$ monohydroxy alkane, particularly methanol, ethanol, i-propanol or a mixture thereof.

Seeding may be applied in step b) or c) to assist or iniciate crystallization.

In a preferred embodiment of this process A, crude, syrupy or amorphous DFL, to be crystallized, is dissolved in an aqueous $C_1$-$C_4$ alcohol between 40 and 70° C., optionally under agitation, until a clear solution is obtained in step a). This solution is allowed to cool to room temperature while stirring is continued for 6-72 hours in step b), during which a $C_1$-$C_4$ alcohol, particularly the same as was used in step a), can be added in step c). The precipitated DFL crystals are collected by filtration, washed with a $C_1$-$C_4$ alcohol and dried in step e). The collected and washed crystalline material is dried:
either on air until constant weight or
under vacuum, preferably at an elevated temperature.

Drying on air lasts typically a week. Vacuum drying can be conducted in a desiccator or vacuum oven typically between 5 and 25 mbar. When heating is applied during vacuum drying, the temperature preferably does not exceed 50° C. and lasts no more than 16 hours.

The overall amount of aqueous $C_1$-$C_4$ alcohol used in crystallizing DFL in steps a), b) and c) is preferably around 2.5-8 volumes (1 volume is 1 ml of solvent or solvent parts per g of DFL to be crystallized), in which the $C_1$-$C_4$ alcohol/water ratio is preferably between 1 and 6 (by volume/volume). Preferably, the crude, syrupy or amorphous DFL is dissolved in step a) in an aqueous $C_1$-$C_4$ alcohol (3-6 volumes) between room temperature and 70° C. to make a solution, to which a further amount of a $C_1$-$C_4$ alcohol can be added, preferably slowly, during step c).

If isopropanol is used as the $C_1$-$C_4$ alcohol, the crude, syrupy or amorphous DFL is preferably dissolved in 3-4 volumes of aqueous isopropanol (isopropanol-water ratio is around 1) or 1-2.5 volumes of water and then 1.5-2 volumes of isopropanol are added at room temperature in step a), the obtained solution is stirred for about 12-24 hours in step b) and the precipitated DFL crystals are collected by filtration, washed with aqueous isopropanol and dried in step d).

If ethanol is used as the $C_1$-$C_4$ alcohol, the crude, syrupy or amorphous DFL is preferably dissolved in 2-7 volumes, especially 2.5-6.5 volumes, of aqueous ethanol (ethanol-water ratio is 1.5-3) or 1-2.5 volumes of water and then 1-4.5 volumes of ethanol are added at 50-70° C. in step a), the obtained solution is cooled down to room temperature and kept at this temperature while being stirred for about 12-50 hours in step b) and a further amount of ethanol (1-3.5 volumes) can be added in steps c) before the precipitated DFL crystals are collected by filtration, washed with aqueous ethanol and dried in step d).

In other preferred embodiment of process A a DFL solution is provided in an aqueous $C_1$-$C_4$ alcohol at room temperature, optionally under agitation, until a clear solution is obtained in step a). This solution is stirred is for 6-72 hours in step b) and a alcohol, particularly the same as was used in step a), is added in step c). The precipitated DFL crystals are collected by filtration, washed with a $C_1$-$C_4$ alcohol and dried in step d).

The aqueous $C_1$-$C_4$ alcohol is preferably a binary mixture of a $C_1$-$C_4$ alcohol and water, wherein the $C_1$-$C_4$ alcohol is advantageously ethanol or isopropanol, or a ternary mixture of two $C_1$-$C_4$ alcohols and water. The overall amount of aqueous $C_1$-$C_4$ alcohol used in crystallizing DFL according to the above process is preferably around 8-16 volumes (1 volume is 1 ml of solvent or solvent parts per g of DFL to be crystallized), in which the $C_1$-$C_4$ alcohol(s)/water ratio is preferably between 2 and 4 (by volume/volume). Preferably, a DFL solution in water (2-3 volumes) is provided at room temperature in step a), to which a $C_1$-$C_4$ alcohol is added, preferably 6-13 volumes and preferably slowly, during step d). When using a ternary mixture of two $C_1$-$C_4$ alcohols and water, the first alcohol is selected from $C_3$-$C_4$ alcohols, preferably isopropanol and the second alcohol is selected from $C_1$-$C_2$ alcohols, preferably methanol. The $C_3$-$C_4$/$C_1$-$C_2$ alcohol ratio in the overall aqueous $C_1$-$C_4$ alcohol at the end of crystallization is between 2-4 (volume/volume) and that in the aqueous $C_1$-$C_4$ alcohol used in step a) to provide a DFL solution is between 1-2 (volume/volume). Preferably, a DFL solution in aqueous $C_1$-$C_2$ alcohol (3-6 volumes) is provided in step a) at room temperature, to which a $C_3$-$C_4$ alcohol is added, preferably 5-10 volumes and preferably slowly, during step c).

In a yet preferred embodiment of process A DFL is crystallized, from an aqueous $C_1$-$C_4$ alcohol containing an organic solvent other than an alcohol, preferably a ketone or an ester. A DFL solution in an aqueous $C_1$-$C_4$ alcohol is provided at room temperature in step a), This solution is stirred is for 6-72 hours and an organic solvent other than an alcohol is added in step c). The precipitated DFL crystals are collected by filtration, washed with a $C_1$-$C_4$ alcohol and dried in step d).

The aqueous $C_1$-$C_4$ alcohol containing an organic solvent other than an alcohol is preferably a ternary mixture in which the $C_1$-$C_4$ alcohol is preferably a $C_1$-$C_2$ alcohol, more preferably methanol, and the organic solvent other than an alcohol is a ketone, preferably acetone, or an ester, preferably an ester of acetic acid, more preferably ethyl or butyl acetate. The overall amount of aqueous $C_1$-$C_4$ alcohol containing an organic solvent other than an alcohol used in crystallizing DFL according to the above process is preferably around 6-20 volumes (1 volume is 1 ml of solvent or solvent parts per g of DFL to be crystallized), in which the ($C_1$-$C_4$ alcohol+organic solvent)/water ratio is preferably between 1.5 and 3.5 (by volume/volume). Preferably, a DFL in an aqueous $C_1$-$C_4$ alcohol not containing an organic solvent other than an alcohol (3-7 volumes, water/$C_1$-$C_4$ alcohol ratio is 1.3-3) is provided in step a) at room temperature, to which the organic solvent other than an alcohol is added (3-13 volumes), preferably slowly, during step c).

Is it advisable, in certain embodiments, to add seeding crystals to facilitate or control the crystallization of DFL. The utilization of seeding crystals is preferable in step b) or c) of process A wherein DFL to be crystallized is produced by a biotechnological way (fermentation) and therefore accompanied by carbohydrate by-products that are prone to co-crystallize with DFL. By addition of seeding crystal the co-crystallization of carbohydrate by-product(s) from the crystallization mixture is avoidable and the selective crystallization of DFL in high purity is possible. However, when the crude DFL is relatively pure, for example after chemical production of DFL, under certain conditions self-nucleation may occur and DFL is obtainable without seeding. Whether or not seeding is necessary for crystallizing out DFL depends on the relative purity of DFL in the crystallization mixture and/or its concentration in given solvent or solvents mixtures. These conditions are further disclosed in details below.

Process A disclosed above, especially when the $C_1$-$C_4$ alcohol is ethanol or isopropanol, preferably ethanol, is preceded by a chemical or biotechnological synthesis of DFL.

Accordingly, crystals of DFL can be obtained by a process B having the following steps:
a) chemically difucosylating a suitably protected 3,2'-dihydroxy-lactose acceptor and then completely deprotecting the resulting compound to obtain DFL;
b) dissolving the crude DFL obtained in step a) at 50-70° C., in 2.5-4 volumes of aqueous ethanol (ethanol-water ratio is 1.8-2.8), or first adding around 1 volume of water then 1.5-3 volumes of ethanol,
c) stirring the mixture obtained produced in step b) and allowing it to cool to room temperature,
d) adding 2-3.5 volumes of ethanol to the mixture produced in step c), and e) collecting and drying the precipitated crystals produced in step e).

Process B disclosed above is suitable to obtain DFL without addition of seeding crystals.

Furthermore, crystals of DFL can also be obtained without seeding by a process B' having the following steps:
a) chemically difucosylating a suitably protected 3,2'-dihydroxy-lactose acceptor and then completely deprotecting the resulting compound to obtain DFL;
b) dissolving the crude DFL obtained in step a), at room temperature, in 3-4 volumes of aqueous isopropanol (isopropanol-water ratio is about 1), or first adding around 1.5-2 volumes of water then 1.5-2 volumes of isopropanol,
c) stirring the mixture obtained produced in step b) for at least one day, preferably at least 18 hours, and
d) collecting and drying the precipitated crystals produced in step c).

In step a) of processes B and B', a straightforward way to get crude DFL is by a double fucosylation of a suitably protected 3,2'-dihydroxy lactose acceptor followed by the removal of the protecting groups. Such a total synthesis is described by Takeo et al. *Carbohydr. Res,* 141, 159 (1985), or Fernandez-Mayoralas et al. *Carbohydr. Res.* 154, 93 (1986).

However, a preferred way of making crude DFL in step a) of processes B and B' involves the hydrogenolysis of a compound of the following formula 1 or a hydrate or solvate thereof, to remove its $R_1$ and $R_2$ (and $R_3$ if present):

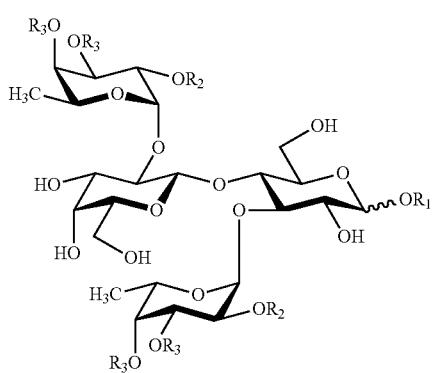

1 wherein $R_1$ and $R_2$ are independently a group removable by hydrogenolysis; and $R_3$ is selected from a group removable by hydrogenolysis and H.

In the description of step a) of processes B and B', the term "group removable by hydrogenolysis" preferably means a protecting group that has a C—O bond with the oxygen of the —$OR_1$, —$OR_2$ and —$OR_3$ groups, and that can be cleaved by hydrogen in the presence of a catalytic amount of palladium, Raney nickel or any other conventional hydrogenolysis catalyst to regenerate the OH group. Such protecting groups are described in Wuts and Greene: Protective Groups in Organic Synthesis, John Wiley & Sons, 2007, and include benzyl, diphenylmethyl (benzhydryl), 1-naphthylmethyl, 2-naphthylmethyl, triphenylmethyl (trityl) and benzyloxycarbonyl groups, each of which can be optionally substituted by one or more of the following groups: alkyl, alkoxy, phenyl, amino, acylamino, alkylamino, dialkylamino, nitro, carboxyl, alkoxycarbonyl, carbamoyl, N-alkylcarbamoyl, N,N-dialkylcarbamoyl, azide, halogenalkyl or halogen. Preferably, such substitution, if present, is on the aromatic ring(s). A preferred protecting group is benzyl or naphthylmethyl optionally substituted with one or more of the following groups: phenyl, alkyl, alkoxy and halogen, more preferably benzyl, 4-methylbenzyl, naphthylmethyl, 4-phenylbenzyl, 4-chlorobenzyl, 4-methoxybenzyl, 3,4-dimethoxybenzyl, 2,4,6-trimethylbenzyl and 2,3,4,5,6-pentamethylbenzyl, particularly unsubstituted benzyl, 4-chlorobenzyl, 3-phenylbenzyl and 4-methylbenzyl groups.

The hydrogenolysis can be carried out in a conventional manner. Preferably, the hydrogenation is carried out by treating the compound of formula 1 with hydrogen in the presence of a catalyst mentioned above in a protic solvent or in a mixture of protic solvents. The protic solvent can be water, acetic acid or a $C_1$-$C_6$ alcohol. A mixture of one or more protic solvents with one or more aprotic organic solvents that are partially or fully miscible with the protic solvent(s), such as THF, dioxane, ethyl acetate or acetone can be used. Water, one or more $C_1$-$C_6$ alcohols, or a mixture of water and one or more $C_1$-$C_6$ alcohols is preferably used as the solvent system. Solutions and suspension containing a compound of formula 1 in any concentrations with the above-mentioned solvent(s) can also be used. The reaction mixture can be stirred at 10-100° C., preferably at 20-50° C., in hydrogen gas atmosphere of 1-50 bar, preferably 5-20 bar. A catalyst concentration of 0.1-5%, preferably 0.5-1%, based on the weight of the compound of formula 1 can be used. Alternatively, transfer hydrogenolysis can be carried out. In this regard, hydrogen can be generated in situ from cyclohexene, cyclohexadiene, formic acid or ammonium formate. The pH of the hydrogenolysis mixture is preferably neutral, but organic or inorganic bases/acids and/or basic and/or acidic ion exchange resins can also be used to improve the kinetics of the hydrogenolysis. The use of basic substances is especially preferred when halogen substituent(s) are present on the substituted benzyl groups of the compound of formula 1. Preferred bases include carbonate and bicarbonate salts, triethylamine, diisopropyl ethylamine, ammonia, ammonium carbamate and diethylamine. An acid can be advantageously used as a co-solvent or additive when multiple benzyl groups have to be removed from the compound of formula 1. Preferred acids include formic acid, acetic acid, propionic acid, chloroacetic acid, dichloroacetic acid, trifluoroacetic acid, HCl and HBr. By this method, DFL can be readily produced in high yield and purity. In this regard, the DFL so produced can be isolated as an amorphous solid by precipitation from water or an organic solvent or an aqueous solution or—after filtration of the catalyst—from the solution in which it was formed from the compound of formula 1. This can be done simply by cooling, or adding an ether such as MTBE, diethyl or diisopropyl ether, a $C_1$-$C_6$ alcohol, acetone or a mixture thereof to the solution. Alternatively DFL can also be isolated by freeze drying and spray drying.

Preferably, compounds of formula 1 are crystalline materials. Crystalline partially benzylated DFL precursors are valuable and highly advantageous final process intermediates for use in making DFL of high purity, especially in a large or industrial scale. Generally, crystallization and/or recrystallization are the simplest and cheapest methods to isolate a product or its precursor from a reaction mixture, separate it from contaminants and obtain it in pure form. Isolation or purification that uses crystallization makes any technological process more efficient. Because $R_1$, $R_2$ and optionally $R_3$ in the compounds of formula 1 are benzyl/substituted benzyl protecting groups, their removal from the compounds can occur nearly quantitatively without significant by-product formation even under gentle hydrogenolysis conditions. These protecting groups are converted exclusively into toluene/substituted toluene during hydrogenolysis, and they can easily be removed from the water soluble DFL via conventional evaporation and/or extraction processes. Thus, the chemical purity of the DFL that can be obtained by process B is comparable to that of the compound of formula 1, from which the DFL is formed.

In preferred compounds of formula 1, $R_1$ is selected from benzyl, 4-methylbenzyl, naphthylmethyl, 4-phenylbenzyl, 4-chlorobenzyl, 4-methoxybenzyl, 3,4-dimethoxybenzyl, 2,4,6-trimethylbenzyl and 2,3,4,5,6-pentamethylbenzyl, more preferably from benzyl and 4-methylbenzyl; $R_2$ is selected from benzyl, 4-methylbenzyl, naphthylmethyl, benzyloxycarbonyl, 4-phenylbenzyl, 4-chlorobenzyl, 4-methoxybenzyl, 3,4-dimethoxybenzyl, 2,4,6-trimethylbenzyl and 2,3,4,5,6-pentamethylbenzyl, preferably from benzyl and 4-methylbenzyl; $R_3$ is selected from benzyl, 4-methylbenzyl, naphthylmethyl, benzyloxycarbonyl, 4-phenylbenzyl, 4-chlorobenzyl, 4-methoxybenzyl, 3,4-dimethoxybenzyl, 2,4,6-trimethylbenzyl, 2,3,4,5,6-pentamethylbenzyl and H, preferably from benzyl, 4-methylbenzyl and H; and —$OR_1$ is in β-orientation. Especially preferred compound of formula 1 is of the following formula 1A:

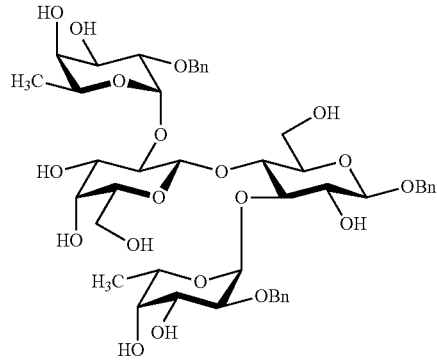

A compound of formula 1 can be made from a compound of the following formula 2

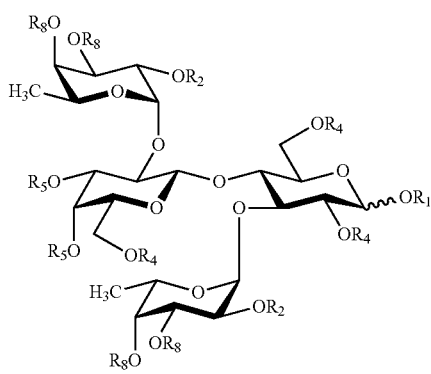

wherein $R_1$ and $R_2$ each are as defined above,
$R_4$ is acyl,
$R_5$ is acyl, or two $R_5$ groups together form a moiety

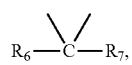

wherein $R_6$ and $R_7$ are independently selected from alkyl and phenyl, or wherein $R_6$ and $R_7$ together with the carbon atom to which they are attached form a cycloalkylidene, and
$R_8$ is selected from a group removable by hydrogenolysis and acyl, or two $R_8$ groups belonging to the same fucosyl residue together form a moiety

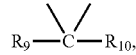

wherein $R_9$ and $R_{10}$ independently are selected from alkyl and phenyl, or wherein $R_9$ and $R_{10}$ together with the carbon atom to which they are attached form a cycloalkylidene,
or a hydrate or solvate thereof,
by a process C comprising the steps of:
a) deacylating the $R_4$ acyl groups and any $R_5$ and $R_8$ acyl groups of the compound of formula 2; and optionally
b) removing any moiety

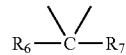

and any moiety

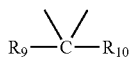

from the compound of formula 2 by treatment with an acid.

In the description of this process C, the term "acyl" in $R_4$, $R_5$ and $R_8$ groups preferably means a Q-C(=O)— moiety, wherein Q can be H, alkyl (a linear or branched chain saturated hydrocarbon group with 1-6 carbon atoms, such as methyl, ethyl, n-propyl, i-propyl, n-butyl, i-butyl, s-butyl, t-butyl, n-hexyl, etc.) or aryl (homoaromatic group such as phenyl or naphthyl), e.g. formyl, acetyl, propionyl, butyryl, pivaloyl, benzoyl, etc. The acyl groups can either be unsubstituted or substituted one or several times, preferably 1-5 times, more preferably 1-3 times. The substituents can be alkyl (for benzoyl), hydroxy, alkoxy, carboxy, oxo (forming a keto or aldehyde function), alkoxycarbonyl, alkylcarbonyl, formyl, aryl, aryloxycarbonyl, aryloxy, arylamino, arylcarbonyl, amino, mono- and dialkylamino, carbamoyl, mono- and dialkyl-aminocarbonyl, alkylcarbonylamino, cyano, alkanoyloxy, nitro, alkylthio and/or halogen (F, Cl, Br, I). Deacylation of the $R_4$ acyl groups and any $R_5$ and $R_8$ acyl groups can be carried out in a conventional manner to remove acyl groups. Acyl groups can be removed in a base catalysed transesterification deprotection reaction, so any acyl protecting groups for hydroxyls are removed in an alcohol solvent such as methanol, ethanol, propanol or t-butanol in the presence of an alcoholate such as NaOMe, NaOEt or KO$^t$Bu at 20-100° C. The alcohol and the alcoholate, should be matched. The use of a co-solvent as toluene or xylene can be beneficial to control particle size of the product and to avoid gel formation. Preferably, a catalytic amount of NaOMe is used in methanol (Zemplén de-O-acylation). Acyl groups can also be removed by a base catalysed hydrolysis in water, an alcohol or a water-organic solvent mixture in homogeneous or heterogeneous reaction conditions at 0-100° C. Preferably, a strong base is used such as LiOH, NaOH, KOH, Ba(OH)$_2$, $K_2CO_3$, a basic ion exchange resin or a tetraalkylammonium hydroxide. In a preferred embodiment, the base is NaOH and the solvent is methanol. By aminolysis, i.e. N-acyl transfer based deprotection, acyl groups can also be removed with ammonia, hydrazine, substituted hydrazine, ethylene diamine or primary amines in water, alcohol or water-organic solvent mixtures at 20-120° C.

With regard to

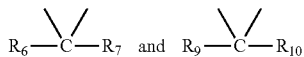

groups, the term "alkyl" preferably means a linear or branched chain saturated hydrocarbon group with 1-6 carbon atoms, such as methyl, ethyl, n-propyl, i-propyl, n-butyl, i-butyl, s-butyl, t-butyl, n-hexyl, etc., and the term "cycloalkylidene" means a bivalent cyclic hydrocarbon ring or group having 3-8 carbon atoms, such as cyclopropylidene, cyclopentylidene, cyclohexylidene, cycloheptylidene, etc.

Any

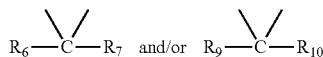

protecting moieties can be removed by treatment with an acid in a conventional manner. By treatment with water acidified to pH>1-2, any such protecting cyclic acetal and/or ketal moieties can be removed simultaneously or successively to regenerate the 1,2-diol(s). Although, the compound of formula 2 also has acyl protecting groups which can also be removed by strong acidic hydrolysis (pH<1-2) and interglycosidic linkages that can also be split by strong acidic hydrolysis (pH<1-2), one skilled in the art can readily select reaction conditions for removing the protecting cyclic acetal or ketal moieties while leaving intact acyl protecting groups and interglycosidic linkages. Water, which serves as a reagent for removing the protecting cyclic acetal or ketal moieties, can also serve as a solvent or co-solvent in this hydrolysis reaction. In this reaction, organic protic or aprotic solvents which are stable under acidic conditions and miscible fully or partially with water, such as $C_1$-$C_6$ alcohols, acetone, THF, dioxane, ethyl acetate or MeCN, can be used in a mixture with water, and with protic acids such as acetic acid, trifluoroacetic acid, HCl, formic acid, sulphuric acid, perchloric acid, oxalic acid, p-toluenesulfonic acid, benzenesulfonic acid or a cation exchange resin in from catalytic amounts to large excesses. The hydrolysis can be carried out at temperatures of 20° C. to reflux until reaching completion which can take about 2 hours to 3 days depending on temperature, concentration and pH. Preferred are: an aqueous solution of an organic acid such as acetic acid, formic acid, chloroacetic acid or perchloric acid used at 20-75° C.; and a $C_1$-$C_6$ alcohol-water-DCM mixture in the presence of HCl, TFA or a sulfonic acid such as p-toluenesulfonic acid or champhorsulfonic acid. Alternatively, an anhydrous $C_1$-$C_6$ alcohol can be used for the cleavage of the acyclic/cyclic acetal/ketal moieties by a trans-acetalization/trans-ketalization process catalysed by an acid such as hydrogen chloride, sulphuric acid, perchloric acid, p-toluenesulfonic acid, acetic acid, oxalic acid, champhorsulfonic acid or a strong acidic ion-exchange at 20° C. to reflux. Preferably, such an acid catalysed mild hydrolysis is carried out in a mixture of water and a $C_1$-$C_6$ alcohol, preferably isopropanol, in the presence of a sulfonic acid, preferably p-toluenesulfonic acid.

Steps a) and b) in the above process C can be carried out in any order. Thus, deacylation of a compound of formula 2, wherein $R_4$, $R_5$ and $R_8$ are independently acyls, leads directly to compounds of formula 1, whereas deacylation of compounds of formula 2, wherein at least one of the

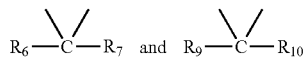

moieties is present, results in the formation of a compound of the following formula 2B

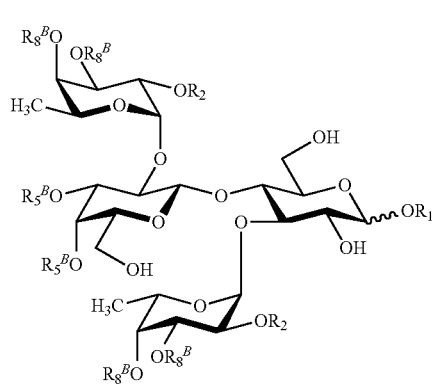

wherein $R_1$ and $R_2$ each are as defined above, $R_5^B$ is H, or two $R_5^B$ groups together form a moiety

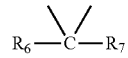

as defined above, and $R_8^B$ is selected from a group removable by hydrogenolysis and H, or two $R_8^B$ groups belonging to the same fucosyl residue together form a moiety

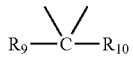

as defined above, provided that at least one

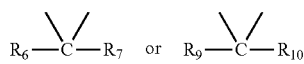

moiety is present.

The compound of formula 2B can then be easily converted by acid treatment into a compound of formula 1.

In a reverse order of deprotection, a compound of formula 2, wherein at least one

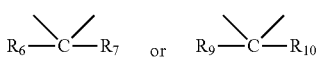

moiety is present, can be subjected to acid treatment to obtain a compound of the following formula 2C

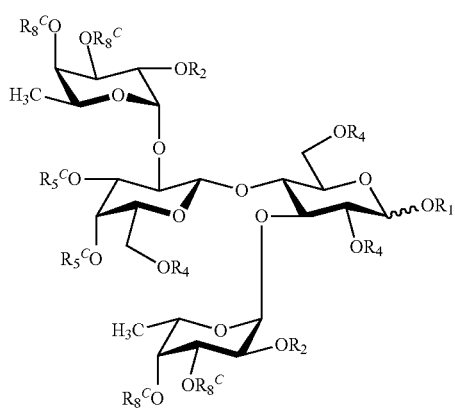

2C wherein $R_1$ and $R_2$ each are as defined above, $R_4$ is acyl, $R_5^C$ is selected from H and acyl, and $R_8^C$ is selected from a group removable by hydrogenolysis, acyl and H, provided that at least one of $R_5^C$ and $R_8^C$ is H.

The compound of formula 2C can then be easily converted by deacylation into a compound of formula 1.

A compound of formula 2 (which is a fully-protected DFL derivative) can be synthesized via a glycosylation process D. Thus, a glycosyl donor of the following formula 3

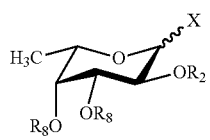

3 wherein $R_2$ and $R_8$ each are as defined above, and

X is selected from a halogen, —OC(=NH)CCl$_3$, —O-pentenyl, —OAc, —OBz and —SR$_{11}$, in which R$_{11}$ is selected from alkyl and optionally substituted phenyl;

can be coupled to a glycosyl acceptor of the following formula 4

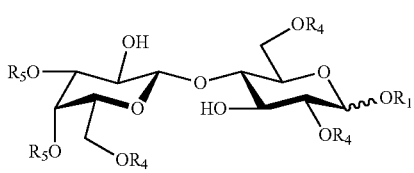

4 wherein $R_1$, $R_4$ and $R_5$ each are as defined above.

This glycosylation process D to produce the compound of formula 2 can be carried out in a conventional manner in an aprotic solvent or in a mixture of aprotic solvents in the presence of an activator. See Demchenko (Ed.): *Handbook of Chemical Glycosylation* Wiley (2008). The glycosylation reaction is generally promoted by heavy metal ions, mainly mercury or silver, and Lewis acids such as trimethylsilyl triflate or BF$_3$-etherate.

Preferably, a glycosyl halide (i.e., X is F, Cl, Br or I) is used in carrying out process D because of its easy accessibility and satisfactory reactivity. Typically, anomeric halides follow the reactivity order F<Cl<Br<I for nucleophilic displacement. Glycosyl fluorides can be prepared by treating the appropriate precursors such as hemiacetals, glycosyl halides, glycosyl esters and S-glycosides with fluorinating reagents such as HF, AgF, AgBF$_4$, tetrabutyl ammonium fluoride, diethylaminosulfur trifluoride, 2-fluoro-1-methyl-pyridinium tosylate, Selectfluor, Deoxo-Fluor or 4-methyl (difluoroiodo)-benzene.

A glycosyl trichloroacetimidate (i.e., X is —OC(=NH) CCl$_3$) can be prepared by adding a sugar with a free anomeric OH to trichloroacetonitrile under inorganic or organic base catalysis. The resulting glycosyl donor can be activated by a catalytic amount of a Lewis acid, such as trimethylsilyl triflate or BF$_3$-etherate, for the glycosylation reaction.

Glycosyl acetates or benzoates (i.e., X is —OAc or —OBz) are preferably first subjected to electrophilic activation to provide a reactive intermediate and then treated with a nucleophilic OH-acceptor. Typical activators of choice are Bronsted acids (e.g., p-TsOH, HClO$_4$ or sulfamic acid), Lewis acids (e.g., ZnCl$_2$, SnCl$_4$, triflate salts, BF$_3$-etherate, trityl perchlorate, AlCl$_3$ or triflic anhydride) or a mixture thereof.

Pentenyl glycosides (i.e. X is —O—(CH$_2$)$_3$—CH=CH$_2$) can be transglycosylated with appropriate glycosyl acceptors in the presence of a promoter such as NBS and NIS. Protic or Lewis acids (triflic acid, Ag-triflate, etc.) can enhance the reaction. The pentenyl glycosides can be prepared with the aid of n-pentenol by standard Fischer glycosylation of hemiacetals under acidic condition, by silver(I) salt promoted coupling of glycosyl bromides (Koenigs-Knorr method), or by glycosylation of 1-acetyl glycosides in the presence of tin(IV) chloride.

Thioglycosides (i.e., X is alkylthio- or optionally substituted phenylthio-group) can be activated by thiofilic promoters such as mercury(II) salts, Br$_2$, I$_2$, NBS, NIS, triflic acid, triflate salts, BF$_3$-etherate, trimethylsilyl triflate, dimethyl-methylthio sulphonium triflate, phenylselenyl triflate, iodonium dicollidine perchlorate, tetrabutylammonium iodide or mixtures thereof, preferably by Br$_2$, NBS, NIS or triflic acid.

Aprotic solvents such as toluene, THF, DCM, chloroform, dioxane, acetonitrile, chlorobenzene, ethylene dichloride, DMSO, DMF or N-methylpyrrolidone or mixtures thereof, preferably DMF, toluene, DCM or mixtures thereof, more preferably toluene or DMF-DCM mixture can be used in this glycosylation reaction at −20 to 20° C., preferably at −10 to 5° C., with reaction time of 5 min to 2 hours. For thiophilic activation, Br$_2$, NBS or NIS can be used, optionally in the presence of triflic acid or a triflate derivative. Usually an excess of donor (>2 eq.) is used compared to the acceptor to ensure bisglycosylation. For quenching the reaction, water or a C$_1$-C$_6$ alcohol is generally used, preferably an aqueous or alcoholic solution of a base like sodium carbonate, sodium bicarbonate, ammonia or triethyl amine, more preferably an aqueous Na$_2$S$_2$O$_3$/NaHCO$_3$ solution.

Preferably, the glycosyl donor is a compound of the following formula 3A

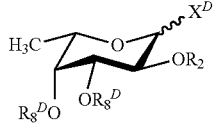

wherein $R_2$ is as defined above,
$R_8^D$ is selected from acyl and a group removable by hydrogenolysis, and
$X^D$ is phenylthio optionally substituted with one or more alkyl.

More preferably $R_2$ is selected from benzyl, 4-methylbenzyl, naphthylmethyl, 4-phenylbenzyl, 4-chlorobenzyl, 4-methoxybenzyl, 3,4-dimethoxybenzyl, 2,4,6-trimethylbenzyl and 2,3,4,5,6-pentamethylbenzyl; $R_8^D$ is selected from benzyl, 4-methylbenzyl, naphthylmethyl, 4-phenylbenzyl, 4-chlorobenzyl, 4-methoxybenzyl, 3,4-dimethoxybenzyl, 2,4,6-trimethylbenzyl, 2,3,4,5,6-pentamethylbenzyl and benzoyl optionally substituted by one or more halogens; and $X^D$ is unsubstituted phenylthio. Even more preferably, $R_2$ is selected from benzyl and 4-methylbenzyl; and $R_8^D$ is selected from benzoyl and 4-chlorobenzoyl.

The glycosyl donors of formula 3 can be made in a conventional manner, e.g. as described in WO 2010/115934 and WO 2010/115935. The acceptors of formula 4 can also be made in a conventional manner, e.g. as described by Tsukida et al. *J. Org. Chem.* 62, 6876 (1997).

The compounds of formulae 2, 2B and 2C above represent crucial intermediates in the total synthesis of DFL. Thus, this invention provides a compound of formula 2A

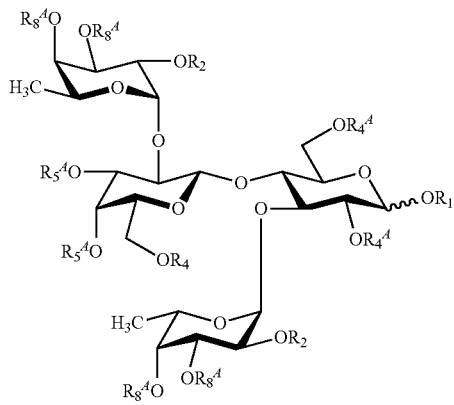

wherein $R_1$ and $R_2$ each are as defined above,
$R_4^A$ is selected from acyl and H,
$R_5^A$ is selected from acyl and H, or two $R_5^A$ groups together form a moiety

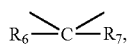

wherein $R_6$ and $R_7$ are as defined above, and
$R_8^A$ is selected from group removable by hydrogenolysis, acyl and H, or two $R_8^A$ groups belonging to same fucosyl residue together form a moiety

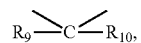

wherein $R_9$ and $R_{10}$ are as defined above,
provided that $R_4^A$, $R_5^A$ and $R_8^A$ are not all H,
or a hydrate or solvate thereof.

Each of the novel derivatives of formula 2A can be considered as a single chemical entity including α and β anomers, as well as an anomeric mixture of α and β isomers. The compounds of formula 2A can be crystalline solids, oils, syrups, precipitated amorphous material or spray dried products. If crystalline, compounds of formula 2A could exist either in anhydrous or hydrated crystalline forms, incorporating one or several molecules of water into their crystal structures. Similarly, the compounds of formula 2A could exist in crystalline forms incorporating ligands such as organic molecules and/or ions into their crystal structures.

Preferably in compounds of formula 2A, $R_1$ is selected from benzyl, 4-methylbenzyl, naphthylmethyl, 4-phenylbenzyl, 4-chlorobenzyl, 4-methoxybenzyl, 3,4-dimethoxybenzyl, 2,4,6-trimethylbenzyl and 2,3,4,5,6-pentamethylbenzyl; $R_2$ is selected from benzyl, 4-methylbenzyl, naphthylmethyl, benzyloxycarbonyl, 4-phenylbenzyl, 4-chlorobenzyl, 4-methoxybenzyl, 3,4-dimethoxybenzyl, 2,4,6-trimethylbenzyl and 2,3,4,5,6-pentamethylbenzyl; $R_4^A$ is selected from acyl and H; $R_5^A$ is selected from acyl and H, or two $R_5^A$ groups together form a moiety

wherein $R_6$ and $R_7$ independently are selected from alkyl and phenyl, or $R_6$ and $R_7$ together with the carbon atom to which they are attached form a cycloalkylidene; and $R_3^A$ is selected from benzyl, 4-methylbenzyl, naphthylmethyl, 4-phenylbenzyl, 4-chlorobenzyl, 4-methoxybenzyl, 3,4-dimethoxybenzyl, 2,4,6-trimethylbenzyl, 2,3,4,5,6-pentamethylbenzyl, acyl and H. More preferably in compounds of formula 2A, $R_1$ and $R_2$ are benzyl; $R_4^A$ is selected from acetyl, pivaloyl, benzoyl, 4-chlorobenzoyl and H; $R_5^A$ is H, or two $R_5^A$ groups together form an isopropylidene or a cyclohexylidene; $R_8^A$ is selected from benzyl, acetyl, pivaloyl, benzoyl, 4-chlorobenzoyl and H; and —$OR_1$, is in β-orientation.

Another preferred way of process A is wherein steps a-d) are preceded by a biotechnological production of DFL. Accordingly, the biotechnological method comprises the steps of:

a) culturing, in an aqueous fermentation broth or culture medium containing lactose or 2'-FL, a genetically modified LacZ⁻Y⁺ *E. coli* containing a recombinant gene that encodes a 1,2-fucosyl transferase, to produce DFL by fucosylating lactose, and then b) separating the aqueous carbohydrate fraction comprising DFL from non-carbohydrate particulates and contaminants of the fermentation broth.

In one embodiment, the fermentation results in a mixture of carbohydrate product in which DFL is in minority. In accordance with WO 01/0434 and M. Randriantsoa: *Synthèse microbiologique des antigènes glucidiques des groupes sanguins*, Theèse de Doctorat soutenue le 30 Sep. 2008 à l' Université Joseph Fourier, Grenoble, France, culturing a genetically modified *E. coli*, containing a recombinant gene that encodes a 1,2-fucosyl transferase, preferably an α1,2-fucosyl transferase, in the presence of lactose can produce very significant amounts of both 2'-FL and DFL in the intra- and the extra-cellular matrix that can be transported to the fermentation broth in a passive way, i.e. can diffuse outside across the cell membrane. Lactose is preferably provided to the culture medium in an amount of at least 50, preferably at least 75, more preferably at least 100 grams of lactose per liter of initial volume of the culture medium, together with a carbon and energy source, preferably glycerol, advantageously in a continuous manner, so that the final volume of the culture medium is not more than three-fold, advantageously not more than two-fold, more advantageously less than two-fold of the volume of the culture medium before the culturing. The $E.\ coli$ is also preferably cultured for at least 4 days, particularly up to 7 days, preferably at a temperature of 30 to 35° C., and preferably with continuous agitation, continuous aeration and continuous feeding of the carbon and energy source and lactose. The resulting fermentation broth contains 2'-FL and DFL as the fucosylated target carbohydrates, and can contain carbohydrate-like contaminants, such as 2-O-fucosyl lactulose, lactose, FFL (Fuc($\alpha$1-2)Fuc($\alpha$1-2)Gal($\beta$1-4)Glc), fucose, glucose and galactose. The broth preferably contains at least 75 grams, more preferably at least 100 grams, particularly up to 115 grams of fucosylated target carbohydrates per liter of the broth. Among these carbohydrates, DFL preferably is at least 2.5%, more preferably at least 5%, even more preferably at least 10%, up to about 20 of the weight of 2'-FL, and among these carbohydrates, 2'-FL is preferably at least 75 w %, more preferably at least 80-85 w % and particularly 85-90 w %. Advantageously, the resulting mixture of 2'-FL and DFL in the culture medium is at least 75, more advantageously at least 100, particularly at least 115 grams per liter of the culture medium.

Preferably, the fucosylated carbohydrates and carbohydrate-like contaminants are then separated from the fermentation broth by the following substeps i)-iii).

Substep i) preferably involves clarifying the aqueous fermentation broth to remove suspended particulates and contaminants, particularly cells, cell components, insoluble metabolites and debris produced by culturing the $E.\ coli$ cell. In this substep i), the fermentation broth, can be clarified in a conventional manner, e.g. by centrifugation and/or filtration.

Substep ii) preferably involves removing substantially all the salts and proteins, as well as peptides, amino acids, RNA and DNA and any endotoxins and glycolipids that could interfere with the subsequent separation step, from the aqueous fermentation broth, preferably after it has been clarified in substep i). In this substep ii), proteins and related impurities can be removed from the fermentation broth in a conventional manner, e.g. by ultrafiltration, tangential flow high-performance filtration, tangential flow ultrafiltration, affinity chromatography, ion exchange chromatography and/or hydrophobic interaction chromatography.

Substep iii) preferably involves concentrating the aqueous solution from substep ii) by about 50-75%, preferably 60-70%. This substep iii) can be carried out in a conventional manner, e.g. by distilling off water at reduced pressure (20-100 mbars) and at ambient temperature up to 40-60° C. or by nanofiltration. The resulting concentrate then preferably contains 35-80 w/w %, preferably 40-68 w/w %, more preferably 45-60 w/w %, particularly 50-56 w/w % of total carbohydrates, including 2'-FL, DFL and other fucosylated and non-fucosylated carbohydrates. The proportion of 2'-FL in the carbohydrate mass of the resulting aqueous concentrate is more than around 80%, more preferably more than about 85% and particularly about 90%. The 2'-FL/DFL ratio in this carbohydrate mass is around 8:1 to 12:1 by weight.

Preferably, most of the 2'-FL in the resulting concentrate is then crystallized out selectively while DFL remains in the mother liquor. Preferably, this involves slowly adding a $C_1$-$C_4$ alcohol, preferably methanol, at 40-60° C., preferably 45-55° C. to the concentrate at about the same temperature. The obtained mixture is then stirred and allowed to cool to room temperature while spontaneous crystallization of 2'-FL occurs. This crystallization can be expedited by adding seeding crystals to the broth. Preferably, the volume of the $C_1$-$C_4$ alcohol added to the concentrate, in one, two or even more portions, is about 4-8 times, preferably about 5-7 times relative to the weight of 2'-FL in the concentrate.

DFL is then crystallized from the remaining mother liquor, preferably by first crystallizing most of the residual 2'-FL selectively and then crystallizing DFL from the remainder of the mixture.

Most of the residual 2'-FL is crystallized from the remaining mother liquor by first concentrating it to be 50-80 w/w %, more preferably 55-70 w/w %, particularly around 60-68 w/w %, of total carbohydrates containing 48-65% 2'-FL in with a 2'-FL/DFL ratio of around 1:1 to 2:1 by weight. Then, a $C_1$-$C_4$ alcohol, preferably the same alcohol as before, is slowly added at 40-60° C., preferably 50-60 to the concentrated remaining mother liquor which is then stirred at the same temperature and then allowed to cool to room temperature while spontaneous crystallization of 2-'FL occurs. This crystallization can be expedited by adding 2-'FL seeding crystals. Preferably, the volume of the $C_1$-$C_4$ alcohol added to the concentrated remaining mother liquor, in one, two or even more portions, is about 5-8.5 times relative to the weight of 2'-FL. The second mother liquor contains DFL/2'-FL in a ratio about 4-5:1.

Preferably, DFL is crystallized from the concentrated, preferably freeze dried, second mother liquor by a process E comprising the steps of:
a) dissolving the concentrated mother liquor containing DFL, preferably at 50-70° C. by adding 6-7 volumes of aqueous ethanol (ethanol-water ratio is 1.5-2) to it, or first adding 2-2.5 volumes of water and then 4.5-5.5 volumes of ethanol,
b) stirring the mixture from step a) and then allowing it to cool to room temperature,
c) then adding seeding crystal of DFL to the mixture from step b) to assist in the crystallization,
d) optionally adding a further 0.5-1.5 volumes of ethanol to the mixture from step b) or c), and
e) collecting and drying the precipitated DFL crystals from step d).

In other embodiment, the biotechnological method of step a) above is conducted that the fermentation results in a mixture of carbohydrate products in which DFL is the major compound. This can be done by a genetically modified LacZ$^-$Y$^+$ $E.\ coli$ containing recombinant genes that encode an $\alpha$1,2-fucosyl and an $\alpha$1,3-fucosyl transferase and culturing it in the presence of lactose, for example as disclosed in WO 2012/112777. The fucosylated carbohydrates and carbohydrate-like contaminants are separated from the fermentation broth by substeps i)-iii) disclosed above with the difference that substep iii) involves concentrating the aqueous solution from substep ii), e.g. by distilling off water at reduced pressure (20-100 mbars) and at ambient temperature up to 40-60° C. or by nanofiltration, to obtain a mixture containing 20-50 w/w %, preferably 25-45 w/w %, more preferably 30-40 w/w %, of total carbohydrates, including DFL, 2'-FL, 3-FL and other fucosylated and non-fucosylated carbohydrates such as lactose. The proportion of 2'-FL in the carbohydrate mass of the resulting aqueous concentrate is more than around 70%, more preferably more than about 75% and particularly about 80% (by weight), and this carbohydrate mass does not contain lactose in more than about 10% (by weight).

Preferably, DFL is crystallized from the so-obtained concentrated aqueous mixture by adding, to the concentrated mixture containing DFL at room temperature, 2-7, preferably 4-5 volumes of ethanol (compared to the volume of water of the starting mixture) in portions, during which preferably seeding crystal of DFL is also added to assist the crystallization, or 0.25-0.75, preferably around 0.5 volumes of methanol (compared to the volume of water of the starting mixture) followed by the addition of isopropanol (3-6 volumes, preferably 3-6 volumes compared to the volume of water of the starting mixture) in portions during which preferably seeding crystal of DFL is also added to assist the crystallization.

The total crystallization time is 1-3 day, preferably around 2 days.

Yet an embodiment in which the biotechnological method of step a) above provides a mixture of carbohydrate products with dominant content is fermenting, in an aqueous broth or culture medium containing 2'-FL and a genetically modified $LacZ^-Y^+$ E. coli comprising a recombinant gene that encodes a 1,2-fucosyl transferase, e.g. as disclosed in WO 2015/032413. The fucosylated carbohydrates and carbohydrate-like contaminants are separated from the fermentation broth by substeps i)-iii) disclosed above with the difference that substep iii) involves concentrating the aqueous solution from substep ii), e.g. by distilling off water at reduced pressure (20-100 mbars) and at ambient temperature up to 40-60° C. or by nanofiltration, to obtain a mixture containing 20-50 w/w %, preferably 25-35 w/w %, of total carbohydrates, including DFL, 2'-FL, and other fucosylated and non-fucosylated carbohydrates. The proportion of 2'-FL in the carbohydrate mass of the resulting aqueous concentrate is more than around 70%, more preferably more than about 75% and particularly about 80% (by weight). The DFL/2'-FL ratio in this carbohydrate mass is around 3:1 to 12:1 by weight.

Preferably, DFL is crystallized from the so-obtained concentrated aqueous mixture and containing DFL and 2'-FL in a ratio of about 3.5:1 to 4.5:1 by adding, to the concentrated mixture containing DFL at room temperature, 0.25-0.75 volumes of methanol (compared to the volume of water of the starting mixture) followed by the addition of an organic solvent different than an alcohol, preferably a ketone, particularly acetone (3-8 volumes compared to the volume of water of the starting mixture) in portions during which preferably seeding crystal of DFL is also added to assist the crystallization. The total crystallization time is typically 1-2 days.

In addition, the invention relates to the chemical total synthesis of DFL comprising the step of hydrogenolysis of a compound of formula 1 or a hydrate or solvate thereof

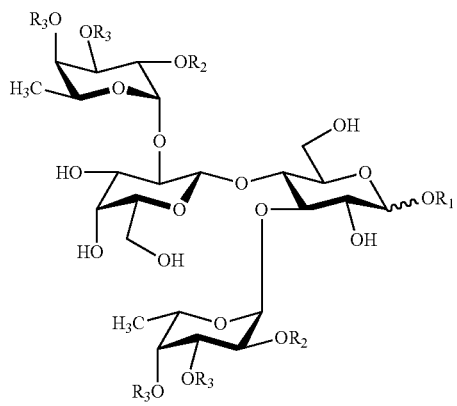

1 wherein $R_1$ and $R_2$ are independently a group removable by hydrogenolysis; and $R_3$ is selected from a group removable by hydrogenolysis and H, preferably H.

Preferably, the compound of formula 1 is made from a compound of formula 2

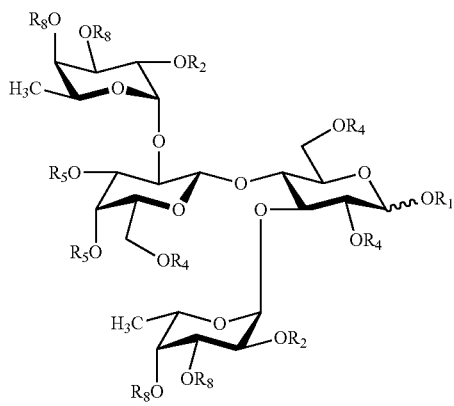

2 wherein $R_1$ and $R_2$ each are as defined above, $R_4$ is acyl, $R_5$ is acyl, or two $R_5$ groups together form a moiety

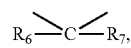

wherein $R_6$ and $R_7$ are independently selected from alkyl and phenyl, or wherein $R_6$ and $R_7$ together with the carbon atom to which they are attached form a cycloalkylidene, and $R_8$ is selected from a group removable by hydrogenolysis and acyl, or two $R_8$ groups belonging to the same fucosyl residue together form a moiety

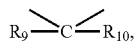

wherein $R_9$ and $R_{10}$ independently are selected from alkyl and phenyl, or wherein $R_9$ and $R_{10}$ together with the carbon atom to which they are attached form a cycloalkylidene, or a hydrate or solvate thereof comprising the steps of:

a) deacylating the $R_4$ acyl groups and any $R_5$ and $R_6$ acyl groups of the compound of formula 2; and optionally b) removing any moiety

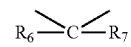

and any moiety

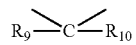

from the compound of formula 2 by treatment with an acid.

The compound of formula 2 is synthesized from a glycosyl donor of formula 3

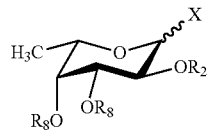

wherein $R_2$ and $R_8$ each are as defined above, and
X is selected from a halogen, —OC(=NH)CCl$_3$, —O-pentenyl, —OAc, —OBz and —SR$_{11}$, in which R$_{11}$ is selected from alkyl and optionally substituted phenyl;
and a glycosyl acceptor of formula 4

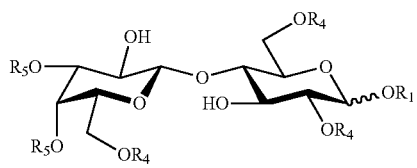

wherein $R_1$, $R_4$ and $R_5$ each are as defined above, via glycosylation.

The steps of making DFL chemically from compounds of formula 3 and 4 via compound of formula 2 then 1 are disclosed in detailed form in step a) of process B, and in steps of process C and D above.

Other features of the invention will become apparent from the following examples which illustrate the invention but do not limit it.

EXAMPLES

Example 1—Producing a Culture Medium Containing 2'-FL+DFL

Bacterial strains and inoculum preparation:

Engineered *E. coli* was constructed from *E. coli* K strain in accordance with WO 01/04341 and Drouillard et al. *Angew. Chem. Int. Ed. Eng.* 45, 1778 (2006), by deleting genes that are liable to degrade lactose, the oligosaccharide products and their metabolic intermediates, inter alia the lacZ, lacA and wcaJ genes, maintaining manB, manC, gmd and wcaG genes involved in the GDP-fucose biosynthesis, and inserting *H. pylori* futC gene for α-1,2-fucosyl transferase, as only glycosyl transferase.

Fermentation Condition:

Glucose, glycerol, isopropyl thio-β-D-galactopyranoside (IPTG) and lactose were each sterilized at 120° C. The culture was carried out in a 3 l fermenter containing 1.5 l of mineral culture medium (Samain et al. *J. Biotechnol.* 72, 33 (1999)). The temperature was kept at 33° C. and the pH regulated at 6.8 with 28% NH$_4$OH. The inoculum (1% of the volume of the basal medium) consisted in a LB medium and the culture of the producing strain. The exponential growth phase started with the inoculation and stopped until exhaustion of the carbon source (glucose 17.5 g/l) initially added to the medium. The inducer (isopropyl thio-β-D-galactopyranoside, IPTG, 1-2 ml of a 50 mg/ml solution) was added at the end of the exponential phase. Then a fed-batch was realized, using 1 l of a feed solution containing 500 g of glycerol and 160-200 g of lactose dissolved in water, which was added to the culture during 4-7 days. At the end of the fermentation, the 2'-FL concentration varied between 68-114 g/l, and the 2'-FL:DFL ratio varied between around 80:20 to 88:12 in the mixture produced. Fucosylated lactulose (2'-O-fucosyl-lactulose) was no more than 1% in this mixture.

Purification of the Broth:

Cells and proteins were removed by ultrafiltration and the obtained solution was concentrated by nanofiltration to around 400 ml (the solution contained ≈93 g of 2'-FL, ≈10.5 g of DFL and ≈0.5 g of lactose). The solution was then treated with charcoal (8 g) to decolorize. The decolorized solution was eluted through a strong cation exchange resin (H$^+$ form) and a weak anion exchange resin (free base form) to demineralise it and catch the remaining colour (eluent: demineralised water). No separation of carbohydrates was observed. The carbohydrate positive fractions were pooled and concentrated to 216 g at reduced pressure (20-30 mbars) at 40° C. The analysis of the resulting almost colourless solution showed no loss of 2'-FL, DFL and lactose by adsorption on the charcoal and the resins.

Example 2—Selective Crystallization of 2'-FL from the Purified and Concentrated Culture Medium Containing 2'-FL+DFL of Example A) To the solution obtained in Example 1 MeOH (280 ml) was added while keeping the temperature at 60° C. 2'-FL seeding crystals were then added and another portion of MeOH (280 ml). After addition of MeOH the stirring was continued at the same temperature for 1 hour, then at 25° C. for 19 hours. The crystallized 2'-FL was filtered off and washed twice with 40 ml of MeOH. The mother liquor and the washing were freeze dried.

36 g from the freeze dried mixture (containing 21.8 g of 2'-FL and 9.2 g of DFL) were dissolved in in water (17.5 ml) and MeOH (22 ml) at 50° C. The solution was cooled to room temperature and 2'-FL seeding crystals were added followed by addition of methanol (110 ml). The crystallization mixture was stirred at room temperature for 17 hours. The crystals were filtered off and washed with MeOH.

B) To the solution obtained in Example 1 MeOH (560 ml) was added while keeping the temperature at 50° C. 2'-FL seeding crystals were then added and the stirring was continued at the same temperature for 1 hour, then at 25° C. for 19 hours. The crystallized 2'-FL was filtered off and washed twice with 40 ml of MeOH. The mother liquor and the washing were freeze dried.

23 g from the freeze dried mixture (containing 10.8 g of 2'-FL and 9.2 g of DFL) were dissolved in in water (8.5 ml) and MeOH (11 ml) at 50° C. The solution was cooled to room temperature and 2'-FL seeding crystals were added followed by addition of methanol (55 ml). The crystallization mixture was stirred at room temperature for 1 hour at room temperature, 30 min at 50° C. and 17 hours at room temperature. The crystals were filtered off and washed with MeOH.

Example 3—Crystallization of DFL from Fermentation Sample

A) The mother liquor and the wash solutions from Example 2A were combined, concentrated and freeze-dried (white solid; 14.5 g; composition by HPLC assay: DFL 8.65 g, 2'-FL 2.0 g). The solid 2.5 was dissolved in water (17 ml) and EtOH (34 ml) was slowly added at rt. The solution was seeded (~20 mg) and stirred at room temperature for 3 days. The crystals were filtered off and washed with 2×5 ml of EtOH/water (4:1) to give 8.78 g of wet solid. It was dried on air until constant weight (7 days, 6.77 g). HPLC assay: 99.9% (rel. area). Water content: 19.9% (Karl Fischer).

B) The mother liquor and the wash solutions from Example 2B were combined, concentrated and freeze-dried (white solid; 14.9 g; composition by HPLC assay: DFL 8.5 g, 2'-FL 2.1 g). The solid was dissolved in water (21 ml) and EtOH (34 ml) was added at 60° C. The solution was cooled to room temperature, seeded (~20 mg) and stirred at room temperature for 3 days. More EtOH (8 ml) was added over 3 hours to the suspension, and stirring was continued for 5 hours more. Crystals were filtered off and washed with 3×5 ml of EtOH/H$_2$O (4:1) to give 7.32 g of wet solid. It was dried on air until constant weight (7 days, 6.25 g). HPLC assay: 97.4% (rel. area). Water content: 16.3% (Karl Fischer).

Example 4—Chemical Production of DFL

Acceptor synthesis:

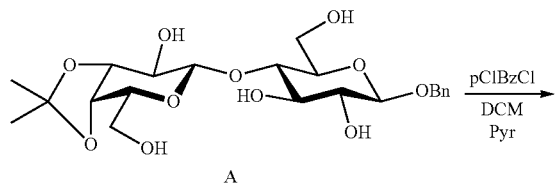

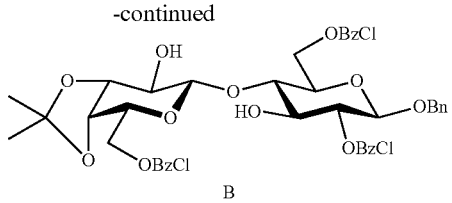

The pentahydroxy benzyl lactoside A (Tsukida et al. *J. Org. Chem.* 62, 6876 (1997), 100 g) was suspended in 300 ml of dichloromethane (DCM) and 100 ml of pyridine. The mixture was cooled to 0° C. and p-chlorobenzoyl chloride (55 ml, 2 equiv.) was added slowly. The temperature was kept between 2-7° C. After completion of the addition the reaction mixture was stirred for 1 hour at 2-7° C., then p-chlorobenzoyl chloride (27.5 ml, 1 equiv.) was added slowly keeping the temperature between 2-7° C. The mixture was stirred for 1 hour at 2-7° C., then again p-chlorobenzoyl chloride (6 ml, 0.22 equiv.) was added slowly keeping the temperature between 2-7° C. The mixture was stirred for 1 hour at 2-7° C. Methanol (2 ml) was added to the mixture under stirring followed by addition of DCM (150 ml). The organic phase was washed with 20% HCl solution (150 ml) and brine, then concentrated in vacuum. Compound B was crystallized from ethyl acetate/hexane or ethyl acetate/MTBE. See $^1$H and $^{13}$C NMR assignments of compound B in Table 2 below (400 MHz, DMSO).

TABLE 2

| Ring | Proton | Shift (ppm) | Mult. | J (Hz) | Carbon | Shift (ppm) |
| --- | --- | --- | --- | --- | --- | --- |
| Glucose (β) | H-1 | 4.82 | d | 8.1 | C-1 | 99.0 |
| | O—CH$_2$—Ph | 4.70 | d | 12.0 | O—CH$_2$—Ph | 69.8 |
| | O—CH$_2$—Ph | 4.54 | d | 12.0 | | |
| | H-2 | 5.04 | dd | 8.9, 8.1 | C-2 | 73.9 |
| | H-3 | 3.90 | ddd | 8.9, 8.8, 2.1 | C-3 | 72.0 |
| | OH | 5.16 | d | 2.1 | | |
| | H-4 | 3.85 | dd | 9.4, 8.8 | C-4 | 80.4 |
| | H-5 | 3.93 | m | | C-5 | 71.8 |
| | H-6x | 4.72 | dd | 12.1, 2.1 | C-6 | 63.5 |
| | H-6y | 4.56 | dd | 12.1, 5.7 | | |
| Glucose (β) | H-1 | 4.51 | d | 8.2 | C-1 | 102.7 |
| | H-2 | 3.33 | ddd | 8.2, 7.0, 5.3 | C-2 | 71.8 |
| | OH | 5.60 | d | 5.3 | | |
| | H-3 | 4.03 | dd | 7.0, 5.8 | C-3 | 79.2 |
| | O—C((CH$_3$)$_2$)—O | 1.43 | s | | O—C((CH$_3$)$_2$)—O | 27.9 |
| | O—C((CH$_3$)$_2$)—O | 1.28 | s | | O—C((CH$_3$)$_2$)—O | 26.1 |
| | | | | | O—C((CH$_3$)$_2$)—O | 109.0 |
| | H-4 | 4.24 | m | | C-4 | 73.0 |
| | H-5 | 4.35 | m | | C-5 | 70.6 |
| | H-6x | 4.59 | dd | 11.9, 2.4 | C-6 | 64.2 |
| | H-6y | 4.24 | m | | | |

Protecting groups are not detailed in the Table.

Fucosylation-deprotection:

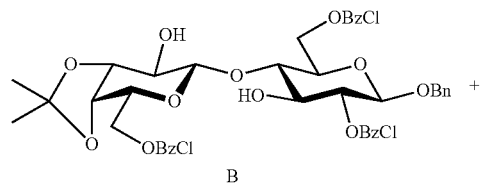

B

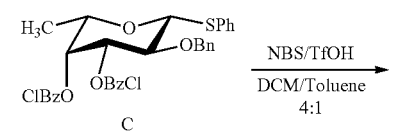

C

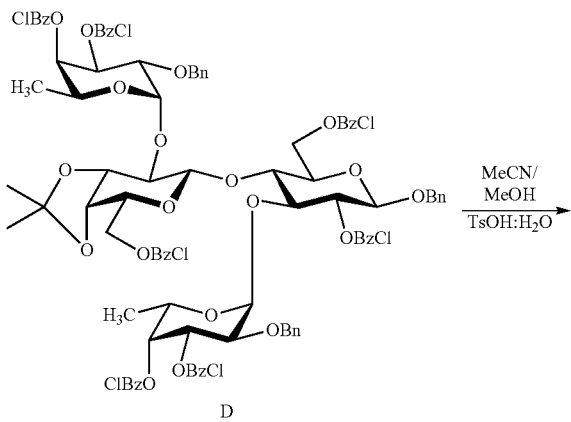

D

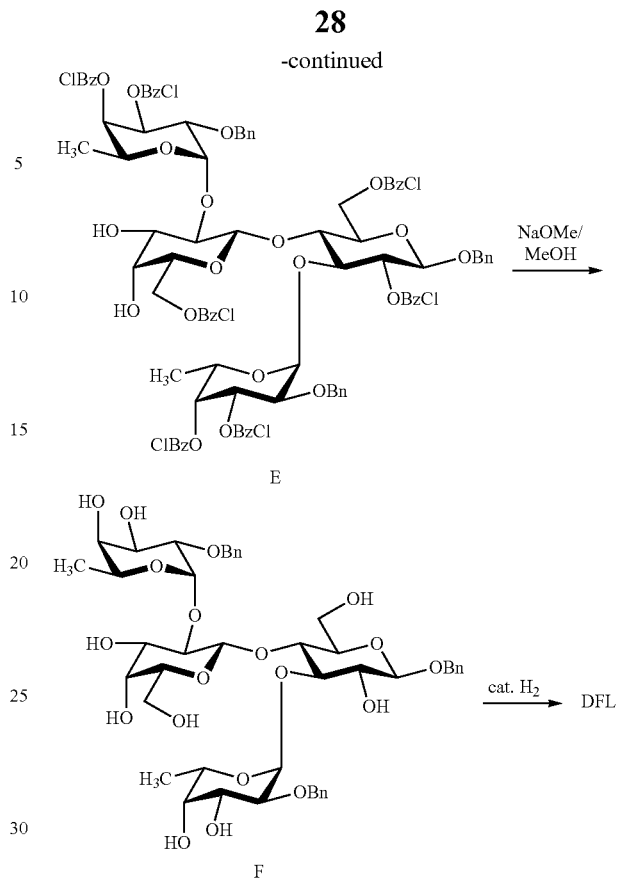

E

F

Acceptor B (73 g) and donor C (WO 2010/115935, 127 g, 2.5 equiv.) were dissolved in DCM/toluene 4:1 (600 ml). The mixture was cooled to −12° C., then NBS (40.2 g) and TfOH (360 µl) were added. The reaction mixture was kept at −5° C. until consumption of donor monitored by TLC. Addition of 25% NH$_4$OH solution (70 ml) quenched the mixture to which water was added (200 ml) and the phases were separated. The organic phase was washed 3 times with water (3×250 ml), dried and concentrated in vacuo to give compound D. See its $^1$H and $^{13}$C NMR assignments in Table 3 below (400 MHz, CDCl$_3$).

TABLE 3

| Ring | Proton | Shift (ppm) | Mult. | J (Hz) | Carbon | Shift (ppm) |
|---|---|---|---|---|---|---|
| Glucose | H-1 | 4.61 | d | 7.9 | C-1 | 98.7 |
|  | O—CH$_2$—Ph | 4.76 | d | 13.2 | O—CH$_2$—Ph | 70.0 |
|  | O—CH$_2$—Ph | 4.57 | d | 13.2 |  |  |
|  | H-2 | 5.49 | dd | 8.7, 7.9 | C-2 | 75.0 |
|  | H-3 | 4.24 | dd | 9.1, 8.7 | C-3 | 75.7 |
|  | H-4 | 4.16 | m |  | C-4 | 75.6 |
|  | H-5 | 3.92 | m |  | C-5 | 73.8 |
|  | H-6x | 5.16 | dd | 12.0, 1.7 | C-6 | 62.7 |
|  | H-6y | 4.64 | dd | 12.0, 3.0 |  |  |
| Galactose | H-1 | 4.56 | d | 8.0 | C-1 | 101.1 |
|  | H-2 | 3.75 | dd | 8.0, 5.4 | C-2 | 76.2 |
|  | H-3 | 4.18 | m |  | C-3 | 79.5 |
|  | O—C((CH$_3$)$_2$)—O | 1.57 | s |  | O—C((CH$_3$)$_2$)—O | 28.1 |
|  | O—C((CH$_3$)$_2$)—O | 1.39 | s |  | O—C((CH$_3$)$_2$)—O | 26.1 |
|  |  |  |  |  | O—C((CH$_3$)$_2$)—O | 110.7 |
|  | H-4 | 4.19 | m |  | C-4 | 73.6 |
|  | H-5 | 4.03 | dd | 8.7, 4.0 | C-5 | 72.2 |
|  | H-6x | 5.03 | dd | 11.9, 4.0 | C-6 | 63.3 |
|  | H-6y | 4.86 | dd | 11.9, 8.7 |  |  |

TABLE 3-continued

| Ring | Proton | Shift (ppm) | Mult. | J (Hz) | Carbon | Shift (ppm) |
|---|---|---|---|---|---|---|
| Fucose-1 (connected to glucose) | H-1 | 5.45 | d | 3.8 | C-1 | 97.3 |
|  | H-2 | 3.93 | dd | 10.5, 3.8 | C-2 | 72.4 |
|  | O—$CH_2$—Ph | 4.39 | d | 12.0 | O—$CH_2$—Ph | 72.4 |
|  | O—$CH_2$—Ph | 4.14 | d | 12.0 |  |  |
|  | H-3 | 5.74 | dd | 10.5, 3.6 | C-3 | 70.8 |
|  | H-4 | 5.61 | dd | 3.6, 1.0 | C-4 | 72.9 |
|  | H-5 | 5.28 | qd | 6.4, 1.0 | C-5 | 64.5 |
|  | H-6 | 1.20 | d | 6.4 | C-6 | 16.3 |
| Fucose-2 (connected to galactose) | H-1 | 5.63 | d | 3.4 | C-1 | 95.1 |
|  | H-2 | 4.08 | dd | 10.7, 3.4 | C-2 | 72.6 |
|  | O—$CH_2$—Ph | 4.66 | m |  | O—$CH_2$—Ph | 72.2 |
|  | O—$CH_2$—Ph |  |  |  |  |  |
|  | H-3 | 5.64 | dd | 10.7, 3.2 | C-3 | 70.2 |
|  | H-4 | 5.70 | dd | 3.2, 1.0 | C-4 | 72.6 |
|  | H-5 | 4.53 | qd | 6.6, 1.0 | C-5 | 65.2 |
|  | H-6 | 1.21 | d | 6.6 | C-6 | 16.1 |

Protecting groups are not detailed in the Table.

The tetrasaccharide D obtained above was dissolved in acetonitrile/methanol 3:1 (400 ml). p-Toluenesulfonic acid monohydrate (13 g) was then added, the reaction mixture was stirred at room temperature overnight, neutralized with $Et_3N$ and evaporated in vacuo. The residue was dissolved in DCM (600 ml) and washed with water (250 ml). The organic phase was concentrated in vacuo and the obtained crude material in MeOH (600 ml) and to which 25% NaOMe in MeOH solution (3 ml) was added. The reaction mixture was stirred at 40° C. for 6 hours then at room temperature for overnight, then neutralized with Amberlite IR 120H$^+$ resin. The resin was filtered off and some MeOH was removed in vacuo. The solution was washed twice with hexane and concentrated in vacuo. The residue was crystallized from MeOH/iPrOAc to afford the tribenzyl derivative F ($^{13}$C NMR (DMSO, 150 MHz): δ=139.3, 139.0, 137.7, 128.0, 127.9, 127.8, 127.7, 127.6, 127.5, 127.3, 127.0, 126.8, 102.2, 100.0, 96.4, 95.6, 76.3, 75.7, 75.5, 75.3, 75.1, 74.7, 74.6, 74.4, 72.5, 71.8, 71.7, 70.0, 69.8, 69.4, 68.7, 67.8, 67.5, 65.4, 64.9, 59.4, 59.0, 16.1).

A sample from the above tribenzyl derivative F (17.36 g) was dissolved in 88 ml of MeOH/$H_2O$ (4:1) in an autoclave. Pd/C catalyst (10%, 1.35 g) was added. The autoclave was filled with $H_2$ (5 bar) and the reaction mixture was stirred at 50° C. for 24 hrs. The catalyst was filtered off, washed with MeOH/$H_2O$ (1:1), and the filtrate was concentrated in vacuo to afford a white syrup. Acetone was added to the syrup which was stirred at 50° C. for 30 mins to form a white precipitate. The solid was filtered and dried to result in the amorphous DFL (12.1 g). See its $^1$H and $^{13}$C NMR assignments in Table 4 below (400 MHz, $D_2O$), which are in good agreement with those reported (Ishizuka et al. *J. Carb. Chem.* 18, 523 (1999)).

TABLE 4

| Ring | proton | δ (ppm) | multiplicity | J (Hz) | Carbon | δ (ppm) |
|---|---|---|---|---|---|---|
| Glucose-α (glu) | H-1 | 5.18 | d | 3.8 | C-1 | 94.8 |
|  | H-2 | 3.78 | m |  | C-2 | 75.5 |
|  | H-3 | 3.92 | m |  | C-3 | 77.5 |
|  | H-4 | 3.86 | m |  | C-4 | 75.3 |
|  | H-5 | 3.92 | m |  | C-5 | 73.5 |
|  | H-6x | 3.92 | m |  | C-6 | 62.5 |
|  | H-6y | 3.84 | m |  |  |  |
| Glucose-β (glu) | H-1 | 4.62 | d | 8.1 | C-1 | 98.7 |
|  | H-2 | 3.49 | dd | 9.5, 8.1 | C-2 | 78.3 |
|  | H-3 | 3.71 | m |  | C-3 | 79.8 |
|  | H-4 | 3.88 | m |  | C-4 | 75.4 |
|  | H-5 | 3.46 | m |  | C-5 | 78.3 |
|  | H-6x | 3.99 | m |  | C-6 | 62.6 |
|  | H-6y | 3.80 | m |  |  |  |
| Fucose-a, connected to α glucose (fu-a) | H-1 | 5.40 | d | 4.0 | C-1 | 101.1 |
|  | H-2 | 3.80 | m |  | C-2 | 70.8 |
|  | H-3 | 3.98 | m |  | C-3 | 72.0 |
|  | H-4 | 3.81 | m |  | C-4 | 74.7 |
|  | H-5 | 4.86 | q | 6.3 | C-5 | 69.3 |
|  | $CH_3$ | 1.24 | d | 6.3 | $CH_3$ | 18.1 |
| Fucose-a, connected to β glucose (fu-a) | H-1 | 5.45 | d | 4.0 | C-1 | 101.0 |
|  | H-2 | 3.80 | m |  | C-2 | 70.8 |
|  | H-3 | 3.98 | m |  | C-3 | 71.9 |
|  | H-4 | 3.80 | m |  | C-4 | 74.7 |
|  | H-5 | 4.87 | q | 6.3 | C-5 | 69.3 |
|  | $CH_3$ | 1.24 | d | 6.3 | $CH_3$ | 18.1 |
| Galactose (ga) | H-1 | 4.49 | d | 7.9 | C-1 | 102.9 |
|  | H-2 | 3.63 | m |  | C-2 | 79.1 |
|  | H-3 | 3.85 | m |  | C-3 | 76.3 |
|  | H-4 | 3.87 | m |  | C-4 | 71.5 |
|  | H-5 | 3.59 | m |  | C-5 | 77.6 |
|  | H-6x | 3.75 | m |  | C-6 | 64.2 |
|  | H-6y | 3.71 | m |  |  |  |
| Fucose-b (fu-b) | H-1 | 5.28 | d | 3.3 | C-1 | 102.1 |
|  | H-2 | 3.81 | m |  | C-2 | 70.8 |
|  | H-3 | 3.78 (3.76) | m |  | C-3 | 72.4 |
|  | H-4 | 3.82 | m |  | C-4 | 74.4 |
|  | H-5 | 4.29 (4.27) | q | 6.3 | C-5 | 69.6 |
|  | $CH_3$ | 1.26 | d | 6.3 | $CH_3$ | 18.2 |

Example 5—Crystallization of DFL from Chemical Sample

A) Tribenzyl DFL (10.0 g) was hydrogenolized as described above to give freeze-dried DFL (7.02 g). It was dissolved back in 7 ml of water, heated to 60° C. and 14 ml of EtOH were added dropwise. The resulting solution was allowed to slowly cool down to room temperature and stirred for 42 hours. Further EtOH (14 ml) was slowly dropped to the suspension which was stirred for 6.5 hours. The crystals were filtered off, washed with 10 ml of EtOH/water (4:1), then 10 ml of EtOH, and dried for 16 hours at 45-50° C. and 10 mbars to give the white crystalline DFL (5.99 g). HPLC assay: 98.6% (rel. area). Water content: 15.3% (Karl Fischer).

B) Tribenzyl DFL (40.0 g) was hydrogenolized as described above to give a concentrated aqueous solution (56 g), to which 20 ml of water and 48 ml of i-PrOH were added and the solution was stirred at rt. for 18 hours. The formed crystals were filtered off and dried for 16 hours at 45-50° C. and 10 mbars to give the white crystalline DFL (7.05 g). HPLC assay: 99.4% (rel. area). Water content: 14.2% (Karl Fischer).

C) Tribenzyl DFL (22.0 g) was hydrogenolized as described above to give a concentrated aqueous solution (31 g), to which 15 ml of ethanol were added slowly at room temperature to prevent precipitation. The solution was heated to 65° C. and 25 ml of EtOH were slowly added. Seed crystals were provided and the reaction mixture was stirred and allowed to cool to it. After 15 hours, more EtOH (50 ml) was slowly added to the suspension, and it was stirred for 8 more hours. The crystals were filtered, washed with 2×20 ml of EtOH and dried for 16 hours at 45-50° C. and 10 mbars to give the white crystalline DFL (14.43 g). HPLC assay: 99.7% (rel. area).

Example 6—XRPD Analysis of DFL Crystals

XRPD investigation was conducted with a Philips PW 1710/PW1820 instrument in transmission geometry, using CuKα radiation made monochromatic by means of a graphite monochromator. D-spacings were calculated from the 2Θ values, based on a wavelength of 1.54186 Å. As a general rule the 2Θ values have an error rate of ±0.2 Å.

FIGS. 1-5 clearly show that the X-ray powder diffraction patterns of the crystalline DFL samples obtained in Examples 3 and 5 are identical.

The invention claimed is:

1. Crystalline difucosyllactose characterized by X-ray powder diffraction reflections, based on a measurement using CuKα radiation, at 11.10±0.20 2Θ, 15.80±0.20 2Θ and 18.38±0.20 2Θ.

2. The crystalline difucosyllactose according to claim 1, wherein the crystalline difucosyllactose contains 2-5 mols of water of hydration per mol of difucosyllactose.

3. A pharmaceutical composition comprising the crystalline difucosyllactose of claim 1 as a pharmaceutically active ingredient, together with a pharmaceutically acceptable carrier.

4. A nutritional composition comprising the crystalline difucosyllactose of claim 1 as a nutritionally active ingredient, in an infant formula or a food supplement.

5. The crystalline difucosyllactose according to claim 1, wherein the crystalline difucosyllactose displays X-ray powder diffraction reflections, based on a measurement using CuKα radiation, at 11.10±0.20 2Θ, 15.80±0.20 2Θ, 18.38±0.20 2Θ and 14.46±0.20 2Θ.

6. The crystalline difucosyllactose according to claim 1, wherein the crystalline difucosyllactose displays X-ray powder diffraction reflections, based on a measurement using CuKα radiation, at 11.10±0.20 2Θ, 15.80±0.20 2Θ, 18.38±0.20 2Θ, 14.46±0.20 2Θ and 16.54±0.20 2Θ.

7. A method for producing crystalline difucosyllactose according to claim 1 comprising the steps of:
a) dissolving non-crystalline difucosyllactose in water or a solvent system containing one or more $C_1$-$C_4$ alcohols and water between room temperature and 80° C. to form a mixture, or providing a difucosyllactose solution in water or a solvent system containing one or more $C_1$-$C_4$ alcohols and water between room temperature and 80° C.,
b) stirring the mixture or solution from step a) and allowing the mixture or solution to cool to room temperature if step a) is performed above room temperature,
c) optionally adding one or more $C_1$-$C_4$ alcohols to the mixture during step b), and
d) collecting and drying precipitated difucosyllactose crystals from the mixture of step b) or c).

8. The method according to claim 7, wherein 2.5-8 volumes $C_1$-$C_4$ alcohol and water per g of difucosyllactose to be crystallized are used, and the $C_1$-$C_4$ alcohol/water volume ratio is between 1 and 6.

9. The method according to claim 7, wherein the $C_1$-$C_4$ alcohol is ethanol or isopropanol.

10. The method according to claim 7 comprising the steps of:
dissolving non-crystalline difucosyllactose at 50-70° C., in 2.5-6.5 volumes of aqueous ethanol, wherein the ethanol-water ratio is 1.5-3, or first adding 1-2.5 volumes of water then 1.5-4 volumes of ethanol, to form the mixture in step a),
cooling the mixture to room temperature in step b),
optionally adding further 1-3.5 volumes of ethanol to the mixture during step c).

11. The method according to claim 10, wherein the non-crystalline difucosyllactose is made by chemical fucosylation of a suitably protected 3,2'-dihydroxy-lactose acceptor followed by complete deprotection.

12. The method according to claim 11, wherein the chemical fucosylation of a suitably protected 3,2'-dihydroxy-lactose acceptor followed by complete deprotection comprises the hydrogenolysis of a compound of formula 1

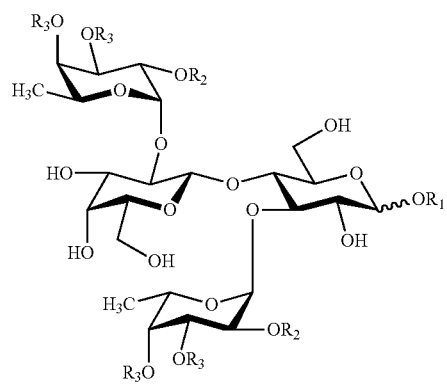

wherein $R_1$ and $R_2$ are independently a group removable by hydrogenolysis; and $R_3$ is a group removable by hydrogenolysis or H.

13. The method according to claim 11 comprising the steps of:
dissolving the non-crystalline difucosyllactose at 50-70° C., in 2.5-4 volumes of aqueous ethanol, wherein the ethanol-water ratio is 1.8-2.8, or first adding around 1 volume of water then 1.5-3 volumes of ethanol in step a),
stirring the mixture and allowing the mixture to cool to room temperature in step b),
adding 2-3.5 volumes of ethanol to the mixture in step c).

14. The method according to claim 7 comprising the steps of:
dissolving non-crystalline difucosyllactose at room temperature, in 3-4 volumes of aqueous isopropanol, wherein the isopropanol-water ratio is about 1, or first adding 1.5-2 volumes of water then 1.5-2 volumes of isopropanol, to form the mixture in step a),
stirring the mixture for 12-24 hours in step b).

15. The method according to claim 14, wherein the non-crystalline difucosyllactose is made by chemical fucosylation of a suitably protected 3,2'-dihydroxy-lactose acceptor followed by complete deprotection.

16. The method according to claim 15 comprising the steps of:
dissolving the non-crystalline difucosyllactose at room temperature, in 3-4 volumes of aqueous isopropanol, wherein the isopropanol-water ratio is about 1, or first adding 1.5-2 volumes of water then 1.5-2 volumes of isopropanol, to form the mixture in step a),
stirring the mixture from step a) for 12-24 hours in step b).

17. The method according to claim 15, wherein the chemical fucosylation of a suitably protected 3,2'-dihydroxy-lactose acceptor followed by complete deprotection comprises the hydrogenolysis of a compound of formula 1

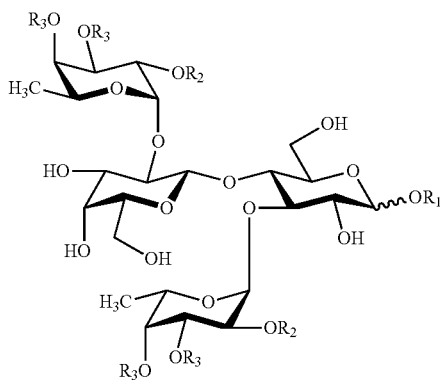

wherein $R_1$ and $R_2$ are independently a group removable by hydrogenolysis; and $R_3$ is a group removable by hydrogenolysis or H.

18. The method according to claim 7 comprising the steps of:
providing a difucosyllactose solution in 2-3 volumes of water at room temperature in step a), and
6-13 volumes of the one or more $C_1$-$C_4$ alcohols are added in step c).

19. The method according to claim 7 comprising the steps of:
providing a difucosyllactose solution in 3-6 volumes of aqueous $C_1$-$C_2$ alcohol at room temperature in step a), and
5-10 volumes of the one or more $C_1$-$C_4$ alcohols are added in step c), wherein the one or more $C_1$-$C_4$ alcohols is $C_3$-$C_4$ alcohol.

20. The method according to claim 7, wherein the difucosyllactose of step a) is made by a biotechnological method comprising the steps of:
culturing, in an aqueous fermentation broth or culture medium containing lactose, a genetically modified LacZ$^-$Y$^+$E. coli containing a recombinant gene that encodes a 1,2-fucosyl transferase, to produce difucosyllactose by fucosylating lactose, and separation of the aqueous carbohydrate fraction comprising difucosyllactose from non-carbohydrate particulates and contaminants of the fermentation broth.

21. The method according to claim 20, wherein the aqueous carbohydrate fraction contains 2'-fucosyllactose and difucosyllactose in which difucosyllactose is at least 2.5% of the weight of 2'-fucosyllactose.

22. The method according to claim 21, wherein the difucosyllactose of step a) is made by a method comprising the steps of:
i) selective crystallization of 2'-fucosyllactose,
ii) dissolving the concentrated mother liquor after step i), at 50-70° C., in 6-7 volumes of aqueous ethanol, wherein the ethanol-water ratio is 1.5-2, or first adding 2-2.5 volumes of water then 4.5-5.5 volumes of ethanol,
iii) stirring the mixture obtained in step ii) and allowing it to cool to room temperature,
iv) adding seeding crystal of DFL to the mixture during step iii) to assist crystallization,
v) optionally adding further 0.5-1.5 volumes of ethanol to the mixture, and
vi) collecting and drying the precipitated crystals from the mixture of step iii) or v).

23. A method for producing crystalline difucosyllactose according to claim 1 comprising the steps of:
a) providing, at room temperature, a difucosyllactose solution in 3-7 volumes of aqueous $C_1$-$C_4$ alcohol not containing an organic solvent other than an alcohol,
b) adding 3-13 volumes of a ketone or an ester and mixing the difucosyllactose solution and the ketone or ester to form a mixture,
c) collecting and drying precipitated difucosyllactose crystals from the mixture.

* * * * *